United States Patent
Rotolo et al.

(10) Patent No.: US 10,450,385 B2
(45) Date of Patent: Oct. 22, 2019

(54) ANTI-CERAMIDE ANTIBODIES

(71) Applicants: MEMORIAL SLOAN-KETTERING CANCER CENTER, New York City, NY (US); CERAMIDE THERAPEUTICS, Brooklyn, NY (US)

(72) Inventors: Jimmy Rotolo, Port Washington, NY (US); Richard Kolesnick, New York City, NY (US)

(73) Assignees: Memorial Sloan Kettering Cancer Center, New York, NY (US); Ceramide Therapeutics, Brooklyn, NY (US)

( * ) Notice: Subject to any disclaimer, the term of this patent is extended or adjusted under 35 U.S.C. 154(b) by 215 days.

(21) Appl. No.: 15/502,162

(22) PCT Filed: Aug. 7, 2015

(86) PCT No.: PCT/US2015/044144
§ 371 (c)(1),
(2) Date: Feb. 6, 2017

(87) PCT Pub. No.: WO2016/022883
PCT Pub. Date: Feb. 11, 2016

(65) Prior Publication Data
US 2017/0335014 A1    Nov. 23, 2017

Related U.S. Application Data

(60) Provisional application No. 62/034,453, filed on Aug. 7, 2014.

(51) Int. Cl.
C07K 16/44    (2006.01)
C07K 16/28    (2006.01)
A61K 39/00    (2006.01)

(52) U.S. Cl.
CPC ............. *C07K 16/44* (2013.01); *C07K 16/28* (2013.01); *A61K 2039/505* (2013.01); *C07K 2317/21* (2013.01); *C07K 2317/24* (2013.01); *C07K 2317/56* (2013.01); *C07K 2317/565* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| 5,331,093 A | 7/1994 | Ishihara et al. |
| 9,090,679 B2 * | 7/2015 | Yokoseki ............... C07K 16/18 |
| 2009/0093438 A1 | 4/2009 | McSwiggen et al. |
| 2010/0034814 A1 | 2/2010 | Sabbandini et al. |
| 2010/0239572 A1 | 9/2010 | Rotolo et al. |
| 2014/0044721 A1 | 2/2014 | Paris et al. |

FOREIGN PATENT DOCUMENTS

| EP | 2 172 219 B1 | 4/2010 |
| JP | 2010-526153 A | 7/2010 |
| RU | 2310393 C1 | 11/2007 |
| WO | WO 2008/137901 | 11/2008 |
| WO | 2013/177596 | 11/2013 |

OTHER PUBLICATIONS

Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
International Search Report and Written Opinion, issued in International Patent Application No. PCT/US15/44144, dated Jan. 14, 2016.
Rotolo, J., et al., "Anti-Ceramide Antibody Prevents The Radiation Gastrointestinal Syndrome In Mice," J. Clin. Invest., May 2012, vol. 122, No. 5, pp. 1786-1790.
Cowart, L.A., et al., "Structural Determinants of Sphingolipid Recognition by Commercially Available Anti-Ceramide Antibodies," J. Lipid Res., 2002, vol. 43, pp. 2042-2048.
Ching, Chen et. al., "Enhancement and destruction of antibody function by somatic mutation: unequal occurrence is controlled by V gene combinatorial associations," The EMBO Journal, vol. 14, No. 12, 1995.
Pakula, A.A., et al., "Genetic Analysis of Protein Stability and Function", Annu. Rev. Genet. 1989; 23:289-310.
Rudikoff S. et al., "Single amino acid substitution altering antigen-binding specificity," Proc. Nat. Acad. Sci. USA, 1982, v.79, pp. 1979-1983.

* cited by examiner

Primary Examiner — Sharon X Wen
(74) Attorney, Agent, or Firm — Foley & Lardner LLP

(57) ABSTRACT

Monoclonal antibodies directed to ceramide that inhibit apoptosis are disclosed. Humanized and scFv versions of the antibodies are also disclosed. Methods for prevention or treatment of apoptosis in a subject by administration of the anti-ceramide antibodies are disclosed.

4 Claims, 16 Drawing Sheets
Specification includes a Sequence Listing.

```
VH
FR1                                             CDR1      FR2                  CDR2
EVQLQQSGTVLARPGASVKMSCKASGYTFT NYWMH WVKQRPVQGLEWIG AIYPGDSDTSYNQKFKG  ] SEQ ID NO: 39

FR3                                             CDR3     FR4
KAKLTAVTSTSTAFMELSSLTNEDSAVYYCTG LYYGYD WGQGTTLTVSS

VL
FR1                                             CDR1           FR2             CDR2
DVLMTQTPLTLSVTIGQPASISC KSSQSLIDSDGKTFLN WLLQRPGQSPKRLIY LVSKLDS  ] SEQ ID NO: 40

FR3                                             CDR3    FR4
GVPDRFTGSGSGTDFTLKISRVEAEDLGLYYC WQGTHFPYT FGGGTKLEIK
```

FIG. 1A

```
VH    FR1                                            CDR1     FR2               CDR2
2A2   EVQLQQSGTVLARPGASVKMSCKASGYTFT NYWMH WVKQRPVQGLEWIG AIYPGDSDTSYNQKFKG
      +VQL QSG  +  +PGASVK+SCKASGYTFT +Y+MH WV+Q P QGLEW+G   I P    TSY QKF+G
1-46  QVQLVQSGAEVKKPGASVKVSCKASGYTFT SYYMH WVRQAPGQGLEWMG IINPSGGSTSYAQKFQG

FR3                                            CDR3      FR4
2A2   KAKLTAVTSTSTAFMELSSLTNEDSAVYYCTG LYYGYD WGQGTTLTVSS SEQ ID NO: 39
       +  +T   TSTST +MELSSL  +ED+AVYYC         WGQGTT+TVSS
1-46  RVTMTRDTSTSTVYMELSSLRSEDTAVYYCAR         WGQGTTVTVSS SEQ ID NO: 41

VL    FR1                                 CDR1             FR2              CDR2
2A2   DVLMTQTPLTLSVTIGQPASISC KSSQSLIDSDGKTFLN WLLQRPGQSPKRLIY LVSKLDS
      DV+MTQ+PL+L VT+GQPASISC +SSQSL+ SDG T+LN W  QRPGQSP+RLIY  VS DS
A1    DVVMTQSPLSLPVTLGQPASISC RSSQSLVYSDGNTYLN WFQQRPGQSPRRLIY KVSNWDS

FR3                                   CDR3    FR4
2A2   GVPDRFTGSGSGTDFTLKISRVEAEDLGLYYC WQGTHFPYT FGGGTKLEIKR  SEQ ID NO: 42
      GVPDRF+GSGSGTDFTLKISRVEAED+G+YYC  QGTH+P T FG GTKLEIKR
A1    GVPDRFSGSGSGTDFTLKISRVEAEDVGVYYC MQGTHWP T FGGGTKLEIKR  SEQ ID NO: 43
```

FIG. 1B

Humanized 2A2 Heavy chain sequence

ATGGACTGGACCTGGAGGGTCTTCTGCTTGCTGGCTGTAGCTCCAGGTGCTCACTCCCAGGTGCAGCTTGTGCAGTCT
GGGGCTGAGGTGAAAAAGCCTGGGGCTTCAGTGAAGGTGTCCTGCAAGGCTTCTGGCTACACCTTTACCAACTACTGG
ATGCACTGGGTAAGACAGGCGCCTGGACAGGGTCTGGAATGGATGGGCGCTATTTATCCTGGAGATAGTGATACTAGC
TACAACCAGAAGTTCAAGGGCCGGGTCACAATGACTCGAGACACATCCACCAGCACTGTCTACATGGAGCTCAGCAGC
CTGAGAAGTGAGGACACTGCCGTCTATTACTGTGCACGCCTTTACTACGGCTACGACTGGGGCCAAGGCACCACTGTC
ACAGTCTCCTCAGCCAGCACGAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTGGTGACCGTGCCCTCCAGC
AGCTTGGGCACCCAGACCTACATCTGCAACGTGAATCACAAGCCCAGCAACACCAAGGTGGACAAGAAAGTTGAGCCC
AAATCTTGTGACAAAACTCACACATGCCCACCGTGCCCAGCACCTGAACTCCTGGGGGGACCGTCAGTCTTCCTCTTC
CCCCCAAAACCCAAGGACACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGGCAGCCCCGAGAACCACAG
GTGTACACCCTGCCCCCATCCCGGGATGAGCTGACCAAGAACCAGGTCAGCCTGACCTGCCTGGTCAAAGGCTTCTAT
CCCAGCGACATCGCCGTGGAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAGGGGAACGTCTTCTCATGC
TCCGTGATGCATGAGGCTCTGCACAACCACTACACGCAGAAGAGCCTCTCCCTGTCCCCGGGTAAATGA  SEQ ID NO: 44

MDWTWRVFCLLAVAPGAHSQVQLVQSGAEVKKPGASVKVSCKASGYTFTNYWMHWVRQAPGQGLEWMG**AIYPGDSDTS
YNQKFKGRVTMTRDTSTSTVYMELSSLRSEDTAVYYCARLYYGYDW**GQGTTVTVSSASTKGPSVFPLAPSSKSTSGGT
AALGCLVKDYFPEPVTVSWNSGALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSK
LTVDKSRWQQGNVFSCSVMHEALHNRYTQKSLSLSPG  SEQ ID NO: 45

Red: leader sequence
Black: variable heavy chain sequence
Bold black: CDR sequence
Green: CH1 sequence
Magenta: hinge sequence
Brown: CH2 and CH3 sequence

FIG. 2A

Humanized 2A2 light chain sequence

ATGAGGCTCCCTGCTCAGCTCCTGGGGCTGCTAATGCTCTGGGTCCCAGGATCCAGTGGGGATGTTGTGATGACCCAA
TCTCCACTCTCTTTGCCGGTTACCCTTGGACAACCAGCCTCCATCTCTTGCAAGTCAAGTCAGAGCCTCATAGATAGT
GATGGAAAGACATTTTTGAATTGGTTCCAACAGAGGCCAGGCCAGTCTCCAAGGCGCCTAATCTATCTGGTGTCTAAA
CTGGACTCTGGAGTCCCTGACAGGTTCTCTGGCAGTGGATCAGGGACAGATTTCACTCTGAAAATCAGCAGAGTGGAG
GCTGAGGATGTGGGAGTTTATTATTGCTGGCAAGGTACACATTTTCCGTACACGTTCGGACAGGGGACCAAGCTGGAA
ATAAAA░░░ACGGTGGCTGCACCATCTGTCTTCATCTTCCCGCCATCTGATGAGCAGTTGAAATCTGGAACTGCCTCT
GTTGTGTGCCTGCTGAATAACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGCACCCTGACGCTGAGCAAA
GCAGACTACGAGAAACACAAAGTCTACGCCTGCGAAGTCACCCATCAGGGCCTGAGTTCGCCCGTCACAAAGAGCTTC
AACAGGGGAGAGTGTTAA    SEQ ID NO: 46

MRLPAQLLGLLMLWVPGSSGDVVMTQSPLSLPVTLGQPASISCKSSQSLIDSDGKTFLNWFQQRPGQSPRRLIY**LVSK
LDSGVPDRFSGSGSGTDFTLKISRVEAEDVGVYYCWQGTHFPYT**FGQGTKLEIK░TVAAPSVFIFPPSDEQLKSGTAS
VVCLLNNFYPREAKVQWKVDNALQSGNSQESVTEQDSKDSTYSLSSTLTLSKADYEKHKVYACEVTHQGLSSPVTKSF
NRGEC    SEQ ID NO: 47

Red: leader sequence
Black: variable light chain sequence
Bold black: CDR sequence
Blue: constant kappa light chain sequence

*FIG. 2B*

ANTI-CERAMIDE ANTIBODIES

CROSS-REFERENCE TO PRIOR APPLICATIONS

The present application is a National Stage Application of PCT/US2015/044144, filed Aug. 7, 2015, which claims priority of U.S. Provisional Application No. 62/034,453, filed on Aug. 7, 2014. The entirety of the aforementioned applications is incorporated herein by reference.

SEQUENCE LISTING

The instant application contains a Sequence Listing which has been submitted electronically in ASCII format and is hereby incorporated by reference in its entirety. Said ASCII copy, created on Jul. 21, 2017, is named 115872-1001_SL.txt and is 37,035 bytes in size.

FIELD

This application generally relates to antibodies that inhibit cell death. In particular, the invention relates to inhibition of cell death with antibodies directed to ceramide.

BACKGROUND

Acute Radiation Syndrome (ARS) (sometimes known as radiation toxicity or radiation sickness) is an acute illness caused by irradiation of a large portion of the body by a high dose of penetrating radiation; such as high energy X-rays, gamma rays, and neutrons; in a very short period of time, for example, within a matter of minutes. The major cause of this syndrome is depletion of immature parenchymal stem cells in specific tissues. Examples of people who suffered from ARS are the survivors of the Hiroshima and Nagasaki atomic bombs, the firefighters that first responded after the Chernobyl Nuclear Power Plant event in 1986, and some unintentional exposures to sterilization irradiators. In general, the radiation dose for the induction of ARS is large (i.e., greater than 0.7 Gray (Gy) or 70 rads), although mild symptoms may be observed with doses as low as 0.3 Gy or 30 rads.

Radiation gastrointestinal (GI) syndrome will usually occur with a dose greater than approximately 10 Gy (1000 rads) although some symptoms may occur as low as 6 Gy or 600 rads. Survival is extremely unlikely with this syndrome due to the destructive and irreparable changes in the GI tract and bone marrow. Radiation GI Syndrome typically can be divided into three stages. The prodromal stage manifests within several hours after exposure and symptoms include anorexia, severe nausea, vomiting, cramps, and diarrhea. The latent stage begins after about two days and the patient may appear and feel well, however, cells lining the GI tract, as well as stem cells in the bone marrow, are dying. Less than one week after exposure, the manifest illness stage begins, with symptoms including malaise, anorexia, severe diarrhea, fever, dehydration, and electrolyte imbalance. Death usually occurs within 2 weeks as a result of infection, dehydration, and electrolyte imbalance.

In addition to the treatment of acute radiation syndrome, bone marrow transplantation is currently used to treat a number of malignant and non-malignant diseases including acute and chronic leukemias, myelomas, solid tumors. However, bone marrow transplantation frequently evokes a variety of immune responses in the host, which results in rejection of the graft or graft-versus-host disease (hereinafter, referred to as "GvHD"). The conditioning regimen required prior to transplantation, designed to ablate or suppress the patient's immune system, renders the patient susceptible to neoplastic relapse or infection. Recent use of unrelated and HLA non-identical donors has unfortunately increased the incidence of GvHD. While removal of T cells from the donor marrow graft ameliorates GvHD, this strategy increases graft failure rates and markedly diminishes the therapeutically-beneficial graft-versus-tumor effect. As such, overall survival does not improve. Further, despite strong pre-clinical data, attempts to improve GvHD outcomes by diminishing inflammatory cytokine action by adding TNF antagonists to corticosteroids, the standard of care for acute GvHD, has provided limited therapeutic benefit.

Thus, there is an urgent need for alternative strategies to reduce the incidence and severity of Radiation GI Syndrome and GvHD.

SUMMARY

One aspect of the present application is directed to an anti-ceramide antibody, or an antigen-binding fragment thereof, comprising: a heavy chain variable region CDR1 of 10 amino acids comprising a Gly in the 1st position from the N-terminal, a Tyr or Phe in the 2nd position from the N-terminal, a Phe or Leu in the 4th position from the N-terminal, and a Thr or His in the 6th position from the N-terminal and a His or Asn in the 10th position from the N-terminal; a heavy chain variable region CDR2 of 16-17 amino acids comprising a Asn or Ile in the 2nd position from the N-terminal, a Phe or Ser in the 4th position from the N-terminal, a Thr in the 9th position from the C-terminal, a Tyr in the 7th position from the C-terminal, an Asn in the 6th position from the C-terminal, a Lys or Ala in the 2nd and 4th positions from the C-terminal; a heavy chain variable region CDR3 of 7 to 11 amino acids comprising a Tyr or Thr at the 4th position from the N-terminal; a light chain variable region CDR1 of 10-16 amino acids comprising an Ala or Ser in the 2nd position from the N-terminal, a Ser in the 3rd position from the N-terminal, a Ser or Asp in the 5th position from the N-terminal, and a Tyr, Ser or Phe in the 3th position from the C-terminal; a light chain variable region CDR2 of 7 amino acids comprising a Ser or Asn in the 3rd position from the N-terminal, a Lys or Ser in the 5th position from the N-terminal and a Ser or Asp in the 7th position from the N-terminal; and a light chain variable region CDR3 of 9 amino acids comprising a Gln, Leu or Trp in the 1st position from the N-terminal, a Gln in the 2nd position from the N-terminal, a Pro in the 7th position from the N-terminal and a Thr in the 9th position from the N-terminal.

Another aspect of the present application is directed to an anti-ceramide single-chain variable fragment (scFv) that binds to the same antigenic determinant as the anti-ceramide antibody of the present application. The scFv comprises: a heavy chain variable region CDR1 of 10 amino acids comprising a Gly in the 1st position from the N-terminal, a Tyr or Phe in the 2nd position from the N-terminal, a Phe or Leu in the 4th position from the N-terminal, and a Thr or His in the 6th position from the N-terminal and a His or Asn in the 10th position from the N-terminal; a heavy chain variable region CDR2 of 16-17 amino acids comprising an Asn or Ile in the 2nd position from the N-terminal, a Phe or Ser in the 4th position from the N-terminal, a Thr in the 9th position from the C-terminal, a Tyr in the 7th position from the C-terminal, an Asn in the 6th position from the C-terminal, a Lys or Ala in the 2nd and 4th positions from the C-terminal; a heavy chain variable region CDR3 of 7 to 11 amino acids comprising a Tyr or Thr at the 4th position from the N-terminal; a light chain variable region CDR1 of 10-16 amino acids comprising an Ala or Ser in the 2nd position from the N-terminal, a Ser in the 3rd position from the N-terminal, a Ser or Asp in the 5th position from the N-terminal, and a Tyr, Ser or Phe in the 3th position from the C-terminal; a light chain variable region CDR2 of 7 amino acids comprising a Ser or Asn in the 3rd position from the N-terminal, a Lys or Ser in the 5th position from the N-terminal and a Ser or Asp in the 7th position from the N-terminal; and a light chain variable region CDR3 of 9 amino acids comprising a Gln, Leu or Trp in the 1st position from the N-terminal, a Gln in the 2nd position from the N-terminal, a Pro in the 7th position from the N-terminal and a Thr in the 9th position from the N-terminal.

Another aspect of the present application is directed to a method of inhibiting cell death in a subject in need thereof, comprising administering to the subject a therapeutically effective amount of the anti-ceramide antibody or an anti-ceramide antibody fragment of the present application.

Yet another aspect of the present application is directed to a method of treating Radiation GI Syndrome or ameliorating a symptom of Radiation GI Syndrome in a subject, comprising administering to the subject a therapeutically effective amount of the anti-ceramide antibody or an anti-ceramide antibody fragment of the present application.

Still another aspect of the present application relates to a method for the mitigation of cell death in GI syndrome in a subject in need thereof. The method comprises administration of an effective amount of an anti-ceramide antibody, or antigen binding fragment thereof, after exposure of said subject to penetrating radiation.

Still another aspect of the present invention relates to a method for the inhibition of apoptosis in GvHD in a subject in need thereof. The method comprises administration of an effective amount of an anti-ceramide antibody, or antigen binding fragment thereof, before said subject receives a transplant or after said subject receives a transplant, but before the onset of GvHD. In another aspect of the present invention, said transplant is a bone marrow transplant.

BRIEF DESCRIPTION OF THE DRAWINGS

The accompanying drawings illustrate one or more embodiments of the present disclosure and, together with the written description, serve to explain the principles of exemplary embodiments of the present disclosure.

FIGS. 1A-B show: (A) the variable heavy (VH) and light chain (VL) sequences of mAb 2A2 (SEQ ID NOS 39-40, respectively, in order of appearance), and (B) amino acid sequence alignment of 2A2 clone and human germline sequence (SEQ ID NOS 39, and 41-43, respectively, in order of appearance).

FIGS. 2A-B show: (A) humanized 2A2 heavy chain sequence (SEQ ID NOS 44-45, respectively, in order of appearance), and (B) humanized 2A2 light chain sequence (SEQ ID NOS 46-47, respectively, in order of appearance).

DETAILED DESCRIPTION

Figure 3:
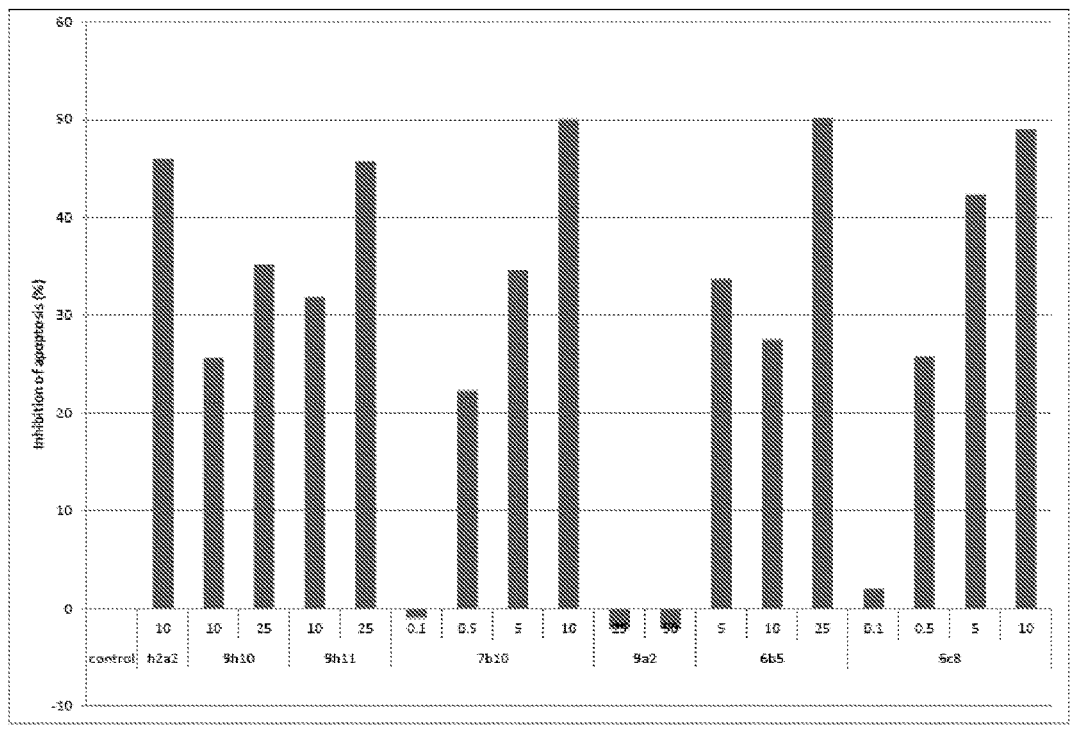
FIG. 3 is an illustration of a biological activity for h2A2, 9H10, 9H11, 7B10, 9A2, 6B5, and 6C8 in vitro using crude supernatant.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

A "therapeutically effective amount," as used herein, refers to an amount of a compound is an amount that achieves the desired biologic or therapeutic effect, namely an amount that prevents, reduces or ameliorates one or more symptoms of the enumerated diseases being treated or prevented.

The terms "treat," "treating" or "treatment" as used herein, refers to a method of alleviating or abrogating a disorder and/or its attendant symptoms. The terms "prevent," "preventing" or "prevention," as used herein, refer to a method of barring a subject from acquiring a disorder and/or its attendant symptoms. In certain embodiments, the terms "prevent," "preventing" or "prevention" refer to a method of reducing the risk of acquiring a disorder and/or its attendant symptoms.

As used herein, the terms "mitigate," "mitigation" and "mitigating," in regard to a treatment, refer to the treatment of an acute event after the occurrence of said event, for example, mitigating radiation damage 24 hours post exposure.

Similarly, as used herein, the terms "protect," "protection" and "protecting," in regard to a treatment, refer to the prophylactic administration of a therapeutic agent for the prevention or inhibition of an event prior to the occurrence of said event.

As used herein, the term "antibody" refers to immunoglobulin molecules and immunologically active portions of immunoglobulin (Ig) molecules, i.e., molecules that contain an antigen binding site that specifically binds (immunoreacts with) an antigen. The term "antibody" is used in the broadest sense and specifically covers monoclonal antibodies (including full length monoclonal antibodies), polyclonal antibodies, multispecific antibodies (e.g., bispecific antibodies), recombinant antibodies, such as scFv, and antibody fragments so long as they exhibit the desired biological activity. By "specifically bind" or "immunoreacts with" is meant that the antibody reacts with one or more antigenic determinants of the desired antigen and does not react (i.e., bind) with other antigens, including polypeptides and lipids or binds at much lower affinity with other antigens.

The term "antibody" also includes antibody fragments that comprise a portion of a full length antibody, generally the antigen binding or variable region thereof. Examples of antibody fragments include Fab, Fab', F(ab')2, and Fv fragments; diabodies; linear antibodies; single-chain variable fragment (scFv); and multispecific antibodies formed from antibody fragments. In certain embodiments of the invention, an antibody fragment, rather than an intact antibody, is used to increase tissue penetration or tumor penetration. In other embodiments, antibody fragment are further modified to increase its serum half-life.

The term "monoclonal antibody" as used herein refers to an antibody obtained from a population of substantially homogeneous antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. Methods for making humanized and other chimeric antibodies are known in the art.

"Bispecific antibodies" are antibodies that have binding specificities for at least two different antigens. Methods for making bispecific antibodies are known in the art.

The use of "heteroconjugate antibodies" is also within the scope of the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies can be prepared in vitro using known methods in synthetic protein chemistry, including those involving crosslinking agents.

As used herein, the term "$LD_{50}$" refers to "Lethal Dose, 50%" or "median lethal dose" and is the amount of a substance required to kill 50% of a test population.

Extracellular Ceramide is Required for Radiation-Induced Apoptosis

Lipid rafts, which are distinct plasma membrane microdomains comprised of cholesterol tightly associated with sphingolipids, in particular sphingomyelin, creating a liquid-ordered domain within the liquid-disordered bulk plasma membrane. Rafts differ in their protein and lipid composition from the surrounding membrane, housing signaling molecules including multiple glycosylphosphatidylinositol (GPI)-anchored proteins, doubly-acylated tyrosine kinases of the Src family and transmembrane proteins. In addition, rafts serve as sites that multiple receptors translocate into or out of upon their activation, including the B cell receptor (BCR) upon encountering antigen. Evidence suggests that these translocation events are crucial for multiple signal transduction cascades.

Sphingolipids are structural components of cell membranes and important regulators of signal transduction through the generation of ceramide. C16 ceramide has important roles in differentiation, proliferation and growth arrest. It is also an essential component of apoptotic signaling. Ceramide generation has been identified as requisite for multiple cytokine-, virus/pathogen-, environmental stress-, and chemotherapeutic-induced apoptotic events. In addition, Ceramide-rich regions on the plasma membrane of target cells are critical for sensitivity to cytotoxic T lymphocyte (CTL)-induced cell death.

Treatment and Prevention of the Lethal GI Syndrome

Cycling crypt base columnar (CBC) cells located at positions 1-3 from the bottom of the crypt of Lieberkuhn, have recently been defined as a population of intestinal stem cells. This group of cells proliferates and differentiates incessantly, replenishing the physiologic loss of enterocytes and other differentiated epithelial cells from the villus apex, thus maintaining the anatomical and functional integrity of the mucosa. A complete or near-complete depletion of this compartment appears required to permanently destroy the crypt-villus unit, while surviving stem cell clonogens, albeit even one per crypt, are capable of regenerating a fully functional crypt.

Radiation targets both the gastrointestinal microvasculature and intestinal stem cell compartments. Dysfunction of the microvascular endothelium, detected as apoptosis at four hours following radiation, represents a principle lesion leading to the GI syndrome. Endothelial dysfunction converts lesions to CBCs from sublethal to lethal, resulting in loss of regenerative crypts and promoting GI toxicity. Immunohistochemical and labeling studies with [$^3$H]TdR and BrdUrd revealed that crypt stem cell death does not occur acutely after radiation exposure. Rather, the earliest detectable response is a temporary dose-dependent delay in progression through a late S-phase checkpoint and mitotic arrest, apparently signaled by radiation-induced DNA double strand breaks (dsb). A rapid apoptotic death occurs in growth arrested cells during the first 24 hours post irradiation that, at 12 Gy, equals 33% of the total death. In mammalian cells, DNA dsbs activate pathways of DNA damage recognition and repair, and a coordinated regulation of cell cycle checkpoint activity. The intestinal stem cell mitotic arrest appears to represent a regulated event in this pathway. A mitotic form of death occurs during this second 24 hours, representing 66% of overall death. No significant change in crypt number per intestinal circumference is apparent at this stage although crypt size progressively decreases due to continued normal migration of crypt transit and differentiated cells from the crypt into the epithelial lining of the villus and loss from the villus tip. Resumption of mitotic activity at 12-18 hours is associated with a rapid depletion of crypt stem cell clonogens and reduction in crypt number per circumference.

The lethality of GI stem cell clonogens is best assessed by the number of crypts surviving at 3.5 days after radiation exposure, which decreases exponentially as the dose increases (C. S. Potten and M. Loeffler, Development 110 (4), 1001 (1990), H. R. Withers, Cancer 28 (1), 75 (1971), and J. G. Maj, F. Paris, A. Haimovitz-Friedman et al., Cancer Res 63, 4338 (2003)). Crypts that contain surviving stem cells proliferate at an accelerated rate, producing typical regenerative crypts that split or bud to generate new crypts, until the intestinal mucosa regains a normal architecture. TBI experiments in several mouse models have demonstrated that the number of surviving crypt stem cells after exposure to 8-12 Gy is usually sufficient to support a complete recovery of the mucosa. At higher doses, however, massive stem cell clonogen loss may lead to a near total collapse of the crypt-villus system, mucosal denudation and animal death from the GI syndrome. The threshold dose for inducing the GI death, and the TBI dose producing 50% GI lethality ($LD_{50}$), appear to be strain-specific. Autopsy studies of C57BL/6 mice exposed to TBI revealed that 25% of the mice exposed to 14 Gy and 100% of those exposed 15 Gy succumbed to the GI syndrome at 6.8+/−0.99 days, predicting an $LD_{50}$ for GI death between 14 and 15 Gy. In contrast, the reported $LD_{50}$D6 (the $LD_{50}$ at day 6, serving as a surrogate marker for GI death) for BALB/c mice is 8.8+/−0.72 Gy, 11.7+/−0.22 Gy for BDF1 mice, 12.5+/−0.1 Gy for C3H/He mice, 14.9 Gy (95% confidence limits 13.9-16.0 Gy) for C3H/SPF mice, and 16.4+/−0.2 Gy for B6CF1 mice, indicating a strain-specific spectrum in mouse sensitivity to death from the GI syndrome. Strain variations in the sensitivity of other organs to radiation, such as the bone marrow and lung have also been reported.

Classically, penetrating radiation (IR) was thought to kill cells by direct damage to genomic DNA, causing genomic instability and resulting in reproductive cell death. Haimovitz-Friedman et al. (Cancer Res 63, 4338 (2003)) demonstrated in a nuclei-free system that apoptotic signaling can alternately be generated by the interaction of IR with cellular membranes. Ceramide mediated raft clustering is involved in IR-induced apoptosis and clonogenic cell death. It has long been accepted that the clonogenic compartment of the gastrointestinal (GI) mucosa is the specific and direct target for radiation in inducing GI damage.

One aspect of the present application is directed to an anti-ceramide antibody, or an antigen-binding fragment thereof, comprising: a heavy chain variable region CDR1 of 10 amino acids comprising a Gly in the 1st position from the N-terminal, a Tyr or Phe in the 2nd position from the N-terminal, a Phe or Leu in the 4th position from the N-terminal, and a Thr or His in the 6th position from the N-terminal and a His or Asn in the 10th position from the N-terminal; a heavy chain variable region CDR2 of 16-17 amino acids comprising a Asn or Ile in the 2nd position from the N-terminal, a Phe or Ser in the 4th position from the N-terminal, a Thr in the 9th position from the C-terminal, a Tyr in the 7th position from the C-terminal, an Asn in the 6th position from the C-terminal, a Lys or Ala in the 2nd and 4th positions from the C-terminal; a heavy chain variable region CDR3 of 7 to 11 amino acids comprising a Tyr or Thr at the 4th position from the N-terminal; a light chain variable region CDR1 of 10-16 amino acids comprising an Ala or Ser in the 2nd position from the N-terminal, a Ser in the 3rd position from the N-terminal, a Ser or Asp in the 5th position from the N-terminal, and a Tyr, Ser or Phe in the 3th position from the C-terminal; a light chain variable region CDR2 of 7 amino acids comprising a Ser or Asn in the 3rd position from the N-terminal, a Lys or Ser in the 5th position from the N-terminal and a Ser or Asp in the 7th position from the N-terminal; and a light chain variable region CDR3 of 9 amino acids comprising a Gln, Leu or Trp in the 1st position from the N-terminal, a Gln in the 2nd position from the N-terminal, a Pro in the 7th position from the N-terminal and a Thr in the 9th position from the N-terminal.

As used herein, the term "CDR" refers to the "complementarity determining region" of an immunoglobulin (antibody) molecule. CDRs are part of the variable domain in an antibody where the antibody binds to its specific antigen. CDRs are crucial to the diversity of antigen specificities generated by lymphocytes. There are three CDR per variable domain (i.e., CDR1, CDR2 and CDR3 in the variable domain of the light chain and CDR1, CDR2 and CDR3 in the variable domain of the heavy chain) for a total of 12 CDRs in an IgG molecule and 60 CDRs in an IgM molecule. Within the variable domain, CDR1 and CDR2 are found in the variable (V) region of a polypeptide chain, CDR3 shows the greatest variability as it is encoded by a recombination of the VJ in the case of a light chain region and VDJ in the case of heavy chain regions.

In some embodiments, the heavy chain variable region CDR1 of the anti-ceramide antibody, or antigen-binding fragment thereof, comprises the sequence GYTFTDHTIH (SEQ ID NO: 1), said heavy chain variable region CDR2 comprises the sequence YNYPRDGSTKYNEKFKG (SEQ ID NO: 2), a heavy chain variable region CDR3 comprising the sequence GFITTVVPSAY (SEQ ID NO: 3), said light chain variable region CDR1 comprises the sequence RASKSISKYLA (SEQ ID NO: 4), a light chain variable region CDR2 comprising the sequence SGSTLQS (SEQ ID NO: 5), and said light chain variable region CDR3 comprising the sequence QQHNEYPWT (SEQ ID NO: 6).

In further embodiments, the anti-ceramide antibody, or antigen-binding fragment thereof, comprises: a heavy chain variable region sequence comprising the sequence QVQLQQSDAELVKPGASVKISCKVSGYTFTDHTIHW-MKQRPEQGLEW IGYNPRDGSTKYNEKFGKATLT-DADKSSSTAYMQLNSLTSEDSAVYFCAKGFITTVV PSAYWGQGTLVTVSA (SEQ ID NO: 7), or a sequence with at least about 80%, 85%, 90% or 95% sequence identity to a heavy chain variable region sequence comprising SEQ ID NO: 7; and/or a light chain variable region sequence comprising SEQ ID NO: 8, or a sequence with at least about 80%, 85%, 90% or 95% sequence identity to a light chain variable region sequence comprising the sequence DVQ-ITQSPSYLAASPGETITINCRASKSISKYLAWYQ EKPGKTNKLLIYSGSTLQSGIPSRFSGSGSGTD-FTLTISSLEPEDFAMYYCQQHNEYPW TFGGGTKLEIK (SEQ ID NO: 8).

In other embodiments, the heavy chain variable region CDR1 of the anti-ceramide antibody, or antigen-binding fragment thereof, comprises the sequence GYAFSSYWMN (SEQ ID NO: 9), said heavy chain variable region CDR2 comprises the sequence QIYPGDGDTNYNGKFKG (SEQ ID NO: 10), a heavy chain variable region CDR3 comprising the sequence RCYYGLYFDV (SEQ ID NO: 11), said light chain variable region CDR1 comprises the sequence KASQDINRYLS (SEQ ID NO: 12), a light chain variable region CDR2 comprising the sequence RANRLVD (SEQ ID NO: 13), and said light chain variable region CDR3 comprising the sequence LQYDEFPYT (SEQ ID NO: 14).

In further embodiments, the anti-ceramide antibody, or antigen-binding fragment thereof, comprises: a heavy chain variable region sequence comprising the sequence QVQLQQSGAELVKPGASVKISCKASGYAFSSYWMN-WVKQRPGKGLEWIGQIYPGD GDTNYNGKFKG-KATLTADKSSSTAYMQLSSLTSEDSAVYFCTRRCYYG-LYFDVWGT GTTVTVSS (SEQ ID NO: 15), or a sequence with at least about 80%, 85%, 90% or 95% sequence identity to a heavy chain variable region sequence comprising SEQ ID NO: 15; and/or a light chain variable region sequence comprising the sequence DIKMTQSPSSRYASLG ERVTITCKASQDINRYLSWFQQKPGKSPKTLIYRAN-RLVDGVPSSRFSGSGSGQDYSL TISSLEYEDMGIYY-CLQYDEFPYTFGGGTKLEIK (SEQ ID NO: 16), or a sequence with at least about 80%, 85%, 90% or 95% sequence identity to a light chain variable region sequence comprising SEQ ID NO: 16.

In yet other embodiments, the heavy chain variable region CDR1 of the anti-ceramide antibody, or antigen-binding fragment thereof, comprises the sequence GYTFTSYWMH (SEQ ID NO: 17), said heavy chain variable region CDR2 comprises the sequence YINPSSGYTKYNQFKD (SEQ ID NO: 18), a heavy chain variable region CDR3 comprising the sequence GGYYGFAY (SEQ ID NO: 19), said light chain variable region CDR1 comprises the sequence SASSSVSYMY(SEQ ID NO: 20), a light chain variable region CDR2 comprising the sequence LTSNLAS (SEQ ID NO: 21), and said light chain variable region CDR3 comprising the sequence QQWSSNPLT (SEQ ID NO: 22).

In further embodiments, the anti-ceramide antibody, or antigen-binding fragment thereof, comprises: a heavy chain variable region sequence comprising the sequence QVQLQQSGAELAKPGASVKLSCKASGYTFTSYWM-HWVKQRPGQGLEWIGYINPSSG YTKYNQFKD-KATLTADKSSSTAYMQLSSLTYEDSAVYYCARG-GYYGFAYWGQGT LVTVSA (SEQ ID NO: 23), or a sequence with at least about 80%, 85%, 90% or 95% sequence identity to a heavy chain variable region sequence comprising SEQ ID NO: 23; and/or a light chain variable region sequence comprising the sequence QIVLTQSPAL-MSASP GEKVTMTCSASSSVSYMYWYQQKPRSSPKP-WIYLTSNLASGVPARFSGSGSGTSYSL TISSMEAE-DAATYYCQQWSSNPLTFGAGTKLELK (SEQ ID NO: 24), or a sequence with at least about 80%, 85%, 90% or 95% sequence identity to a light chain variable region sequence comprising SEQ ID NO: 24.

In still other embodiments, the heavy chain variable region CDR1 of the anti-ceramide antibody, or antigen-binding fragment thereof, comprises the sequence GFSLT-GYGVH (SEQ ID NO: 25), said heavy chain variable region CDR2 comprises the sequence VIWSGGSTDYNAAFIS (SEQ ID NO: 26), a heavy chain variable region CDR3 comprising the sequence NYGYDYAMDY (SEQ ID NO: 27), said light chain variable region CDR1 comprises the sequence RASQSIGTSIH (SEQ ID NO: 28), a light chain variable region CDR2 comprising the sequence YASESIS (SEQ ID NO: 29), and said light chain variable region CDR3 comprising the sequence QQSNSWPFT (SEQ ID NO: 30).

In further embodiments, the anti-ceramide antibody, or antigen-binding fragment thereof, comprises: a heavy chain variable region sequence comprising SEQ ID NO: 31, or a sequence with at least about 80%, 85%, 90% or 95% sequence identity to a heavy chain variable region sequence comprising the sequence QVQLKQS-GPGVQPSSLSITCTVS GFSLTSYGVHWVRQSPGK-GLEWLGVIWSGGSTDYNAAFISRLSISKDNSK-SQVFFKM NSLQADDTAIYYCARNYGYDYAMDYWGQGTSVT-VSS (SEQ ID NO: 31); and/or a light chain variable region sequence comprising the sequence DILLTQSPAILS-VSPGERVSF SCRASQSIGTSIHWYQQRTNGSPRL-LIKYASESISGIPSRFSGSGSGTDFTLSINSVESEDI ADYYCQQSNSWPFTFGSGTKLEIK (SEQ ID NO: 32), or a sequence with at least about 80%, 85%, 90% or 95% sequence identity to a light chain variable region sequence comprising SEQ ID NO: 32.

In even other embodiments, the heavy chain variable region CDR1 of the anti-ceramide antibody, or antigen-binding fragment thereof, comprises the sequence GYTFT-NYWMH (SEQ ID NO: 33), said heavy chain variable region CDR2 comprises the sequence AIYPGDSDTSYN-QKFKG (SEQ ID NO: 34), a heavy chain variable region CDR3 comprising the sequence GLYYGYD (SEQ ID NO: 35), said light chain variable region CDR1 comprises the sequence KSSQSLIDSDGKTFLN (SEQ ID NO: 36), a light chain variable region CDR2 comprising the sequence LVSKLDS (SEQ ID NO: 37), and said light chain variable region CDR3 comprising the sequence WQGTHFPYT (SEQ ID NO: 38).

In further embodiments, the anti-ceramide antibody, or antigen-binding fragment thereof, comprises: a heavy chain variable region sequence comprising the sequence EVQLQQSGTVLARPGASVKMSCKASGYTFTNYWM-HWVKQRPVQGLEW IGAIYPGDSDTSYNQKFKG-KAKLTAVTSTSTAFMELSSLTNEDSAVYYCTGLYY-GYD WGQGTTLTVSS (SEQ ID NO: 39), or a sequence with at least about 80%, 85%, 90% or 95% sequence identity to a heavy chain variable region sequence comprising SEQ ID NO: 39; and/or a light chain variable region sequence comprising SEQ ID NO: 40, or a sequence with at least about 80%, 85%, 90% or 95% sequence identity to a light chain variable region sequence comprising the sequence DVLMTQTPLTLSVTIGQPASISCKSSQSLIDSDGKTF LNWLLQRPGQSPKRLIYLVSKLDSGVPDRFTGSGS-GTDFTLKISRVEAEDLGLYYCW QGTHFPYTFGGGT-KLEIK (SEQ ID NO: 40).

In still yet other embodiments, the anti-ceramide antibody, or antigen-binding fragment thereof, comprises: a) a heavy chain variable region sequence comprising a sequence selected from the group consisting of SEQ ID NOs: 7, 15, 23, 31 and 39, or a sequence with at least about 80%, 85%, 90% or 95% sequence identity to a heavy chain variable region sequence comprising a sequence selected from the group consisting of SEQ ID NOs: 7, 15, 23, 31 and 39; and/or a) a light chain variable region sequence comprising a sequence selected from the group consisting of SEQ ID NOs: 8, 16, 24, 32 and 40, or a sequence with at least about 80%, 85%, 90% or 95% sequence identity to a light chain variable region sequence comprising a sequence selected from the group consisting of SEQ ID NOs: 8, 16, 24, 32 and 40.

In particular embodiments, the anti-ceramide antibody is selected from the group consisting of monoclonal antibody, chimeric antibody, humanized antibody, human antibody, recombinant antibody and scFv.

Another aspect of the present application is directed to an anti-ceramide single-chain variable fragment (scFv) that binds to the same antigenic determinant as the anti-ceramide antibody of the present application. The scFv comprises: a heavy chain variable region CDR1 of 10 amino acids comprising a Gly in the 1st position from the N-terminal, a Tyr or Phe in the 2nd position from the N-terminal, a Phe or Leu in the 4th position from the N-terminal, and a Thr or His in the 6th position from the N-terminal and a His or Asn in the 10th position from the N-terminal; a heavy chain variable region CDR2 of 16-17 amino acids comprising a Asn or Ile in the 2nd position from the N-terminal, a Phe or Ser in the 4th position from the N-terminal, a Thr in the 9th position from the C-terminal, a Tyr in the 7th position from the C-terminal, an Asn in the 6th position from the C-terminal, a Lys or Ala in the 2nd and 4th positions from the C-terminal; a heavy chain variable region CDR3 of 7 to 11 amino acids comprising a Tyr or Thr at the 4th position from the N-terminal; a light chain variable region CDR1 of 10-16 amino acids comprising an Ala or Ser in the 2nd position from the N-terminal, a Ser in the 3rd position from the N-terminal, a Ser or Asp in the 5th position from the N-terminal, and a Tyr, Ser or Phe in the 3th position from the C-terminal; a light chain variable region CDR2 of 7 amino acids comprising a Ser or Asn in the 3rd position from the N-terminal, a Lys or Ser in the 5th position from the N-terminal and a Ser or Asp in the 7th position from the N-terminal; and a light chain variable region CDR3 of 9 amino acids comprising a Gln, Leu or Trp in the 1st position from the N-terminal, a Gln in the 2nd position from the N-terminal, a Pro in the 7th position from the N-terminal and a Thr in the 9th position from the N-terminal.

A single-chain variable fragment (scFv) is not actually a fragment of an antibody, but instead is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. The scFv retains the specificity of the original immunoglobulin, despite removal of the constant regions and the introduction of the linker.

In some embodiments, the anti-ceramide antibodies, antigen-binding fragments thereof, or scFv are produced using recombinant DNA technologies. Procedures for the expression and purification of recombinant proteins are well established in the art.

In order to express the anti-ceramide antibody, antigen-binding fragment thereof, or scFv of the present application in a biological system, a polynucleotide that encodes the anti-ceramide antibody, antigen-binding fragment thereof, or scFv is constructed. In certain embodiments, the recombinant polynucleotide is codon optimized for expression in a selected prokaryotic or eukaryotic host cell, such as a bacterial, mammalian, plant or insect cell. To facilitate replication and expression, the polynucleotide can be incorporated into a vector, such as a prokaryotic or a eukaryotic expression vector. Although the polynucleotide disclosed herein can be included in any one of a variety of vectors (including, for example, bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others), most commonly the vector will be an expression vector suitable for generating polypeptide expression products. In an expression vector, the polynucleotide encoding the anti-ceramide antibody, antigen-binding fragment thereof, or scFv is typically arranged in proximity and orientation to an appropriate transcription control sequence (promoter, and optionally, one or more enhancers) to direct mRNA synthesis. That is, the polynucleotide sequence of interest is operably linked to an appropriate transcription control sequence. Examples of such promoters include: the immediate early promoter of CMV, LTR or SV40 promoter, polyhedron promoter of baculovirus, E. coli lac or trp promoter, phage T7 and lambda $P_L$ promoter, and other promoters known to control expression of genes in prokaryotic or eukaryotic cells or their viruses. The expression vector typically also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in E. coli.

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a polypeptide coding sequence, or a portion thereof, is inserted, exogenous translational control signals, including an ATG initiation codon is provided for expression of the anti-ceramide antibody or scFv. The initiation codon is placed in the correct reading frame to ensure translation of the polynucleotide sequence of interest. Exogenous transcriptional elements and initiation codons can be of various origins, both natural and synthetic. If desired, the efficiency of expression can be further increased by the inclusion of enhancers appropriate to the cell system in use.

Expression vectors carrying the anti-ceramide antibody or scFv of the present application can be introduced into host cells by any of a variety of well-known procedures, such as electroporation, liposome mediated transfection, calcium phosphate precipitation, infection, transfection and the like, depending on the selection of vectors and host cells.

Host cells that contain anti-ceramide antibody, antigen-binding fragment thereof, or scFv-encoding nucleic acids are, thus, also a feature of this disclosure. Favorable host cells include prokaryotic (i.e., bacterial) host cells, such as E. coli, as well as numerous eukaryotic host cells, including fungal (e.g., yeast, such as Saccharomyces cerevisiae and Picchia pastoris) cells, insect cells, plant cells, and mammalian cells (such as CHO cells).

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art. A host cell is optionally chosen for its ability to modulate the expression of the inserted sequences or to process the expressed protein in the desired fashion. Such modifications of the protein include, but are not limited to, glycosylation, (as well as, e.g., acetylation, carboxylation, phosphorylation, lipidation and acylation). Post-translational processing for example, which cleaves a precursor form into a mature form of the protein (for example, by a furin protease) is optionally performed in the context of the host cell. Different host cells such as 3T3, COS, CHO, HeLa, BHK, MDCK, 293, WI38, etc. have specific cellular machinery and characteristic mechanisms for such post-translational activities and can be chosen to ensure the correct modification and processing of the introduced, foreign protein.

For long-term, high-yield production of recombinant anti-ceramide antibody, antigen-binding fragment thereof, or scFv polypeptide, stable expression systems are typically used. For example, polynucleotides encoding an anti-ceramide antibody, antigen-binding fragment thereof, or scFv are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding an anti-ceramide antibody, antigen-binding fragment thereof, or scFv are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed anti-ceramide antibody, antigen-binding fragment thereof, or scFv can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps.

In certain examples, the nucleic acids are introduced into vectors suitable for introduction and expression in prokaryotic cells, e.g., *E. coli* cells. In some embodiments, the expression vector is introduced (e.g., by electroporation) into a suitable bacterial host. In another example, a polynucleotide sequence that encodes an anti-ceramide antibody or scFv is introduced into insect cells using a Baculovirus Expression Vector System (BEVS). Similarly, alternative insect cells can be employed, such as SF21 which is closely related to the SF9, and the High Five (Hi5) cell line derived from a cabbage looper, *Trichoplusia ni*.

In yet other embodiments, the anti-ceramide antibody, antigen-binding fragment thereof, or scFv is expressed in vivo by a plasmid vector or a viral vector.

In certain embodiments, the anti-ceramide antibodies, antigen-binding fragments thereof, and scFv are produced by chemical synthesis. Briefly, an anti-ceramide antibody, antigen-binding fragment thereof, or scFv may be synthesized by coupling the carboxyl group or C-terminus of one amino acid to the amino group or N-terminus of another. Due to the possibility of unintended reactions, protecting groups may be necessary. Chemical peptide synthesis starts at the C-terminal end of the peptide and ends at the N-terminus. This is the opposite of protein biosynthesis, which starts at the N-terminal end.

In some embodiments, the anti-ceramide antibodies, antigen-binding fragments thereof, and scFv may be synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is PEGylated. This last amino acid is often referred to as a carboxyl-PEG-amine, carboxyl-PEO-amine, or amine-PEG-acid, whereby the amine is blocked to protect against reaction and the acid is free to react with the amine group from the previously added amino acid in the reaction. PEG (polyethylene glycol) and PEO (polyethylene oxide) are polymers composed of repeating subunits of ethylene glycol and ethylene oxide monomers. In one embodiment, a PEGylated anti-ceramide antibody, antigen-binding fragments thereof, and scFv would have the PEG moiety connected to the histidine residue (H) at the amino-terminus of the polypeptide. In one embodiment, the PEG moiety is 5 to 30 kDa in size. In another embodiment, the PEG moiety is 10 to 20 kDa in size.

In addition to using PEGylated end amino acid during synthesis, an anti-ceramide antibody, antigen-binding fragment thereof, or scFv may be PEGylated by PEGylation. PEGylation is the process of covalent attachment of polyethylene glycol polymer chains to another molecule, normally a drug or therapeutic protein. PEGylation can be achieved by incubation of a reactive derivative of PEG with the target anti-ceramide antibody or scFv. The covalent attachment of PEG to an anti-ceramide antibody or scFv can "mask" the anti-ceramide antibody, antigen-binding fragment thereof, or scFv from the host's immune system (reduced immunogenicity and antigenicity), increase the hydrodynamic size (size in solution) of the anti-ceramide antibody, antigen-binding fragment thereof, or scFv which prolongs its circulatory time by reducing renal clearance. PEGylation can also provide water solubility to hydrophobic proteins.

Method of Inhibiting Apoptosis

Still another aspect of the present application is directed to a method of inhibiting cell death in a subject in need thereof, comprising administering to the subject a therapeutically effective amount of an anti-ceramide antibody, or antigen-binding fragment thereof, of the present application. In some embodiments, the anti-ceramide antibody is an anti-ceramide scFv.

In some embodiments, the cell death is associated with a disease selected from the group consisting of graft versus host disease, radiation disease, GI syndrome and autoimmune disease. In some further embodiments, the disease is radiation disease or GI syndrome and the anti-ceramide antibody, or antigen-binding fragment thereof, is administered before the subject is exposed to radiation.

Another aspect of the present application is directed to a method for the mitigation of cell death in GI syndrome in a subject in need thereof. The method comprises the administration of an effective amount of an anti-ceramide antibody. In some embodiments, the method comprises administering said anti-ceramide antibody to said subject immediately after exposure of said subject to penetrating radiation. In other embodiments, the method comprises administering said anti-ceramide antibody to said subject within one hour after exposure of said subject to penetrating radiation. In still other embodiments, the method comprises administering said anti-ceramide antibody to said subject within 2, 3, 4, 5, 6, 7, 8, 9, 10, 11, 12 or 18 hours after exposure of said subject to penetrating radiation. In a particular embodiment, the method comprises administering said anti-ceramide antibody to said subject within 24 hours after exposure of said subject to penetrating radiation. In other embodiments, the method comprises administering said anti-ceramide antibody to said subject within 30, 36, 42, 48, 54, 60, 66 or 72 hours after exposure of said subject to penetrating radiation. In other embodiments, the method comprises administering said anti-ceramide antibody to said subject within 48, 36, 24, 18, 12, 10, 8, 6, 4, 2 or 1 hour(s), or within 45, 30 or 15 minutes before exposure of said subject to penetrating radiation.

In other further embodiments, the disease is graft versus host disease and the anti-ceramide antibody, or antigen-binding fragment thereof, is administered before the subject receives a transplant. In some embodiments, the transplant is a bone marrow transplant. In still other further embodiments, the anti-ceramide antibody, or antigen-binding fragment thereof, is administered after the subject receives a transplant, but before the onset of graft versus host disease. In even still other further embodiments, the anti-ceramide antibody, or antigen-binding fragment thereof, is administered to a subject in need thereof after the onset of graft versus host disease in an amount effective for the mitigation of apoptosis in graft versus host disease.

Antibody Administration

The antibody, or antigen-binding fragment thereof, may be administered to the subject with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

Antibodies and antigen-binding fragments thereof of the invention can be administered in the usually accepted pharmaceutically acceptable carriers. Acceptable carriers include, but are not limited to, saline, buffered saline, glucose in saline. Solid supports, liposomes, nanoparticles, microparticles, nanospheres or microspheres may also be used as carriers for administration of the antibodies or antigen-binding fragment thereof.

The appropriate dosage ("therapeutically effective amount") of the antibody, or antigen-binding fragment thereof, will depend, for example, on the condition to be treated, the severity and course of the condition, whether the antibody is administered for preventive or therapeutic purposes, previous therapy, the patient's clinical history and response to the antibody, the type of antibody, or antigen-binding fragment thereof, used, and the discretion of the attending physician. The antibody, or antigen-binding fragment thereof, is suitably administered to the patent at one time or over a series of treatments and may be administered to the patent at any time from diagnosis onwards. The antibody, or antigen-binding fragment thereof, may be administered as the sole treatment or in conjunction with other drugs or therapies useful in treating the condition in question.

As a general proposition, the therapeutically effective amount of the antibody, or antigen-binding fragment thereof, administered will be in the range of about 1 ng/kg body weight/day to about 100 mg/kg body weight/day whether by one or more administrations. In a particular embodiments, the range of antibody administered is from about 1 ng/kg body weight/day to about 1 µg/kg body weight/day, 1 ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 pig/kg body weight/day, 1 µg/kg body weight/day to about 10 pig/kg body weight/day, 1 µg/kg body weight/day to about 100 pig/kg body weight/day, 10 pig/kg body weight/day to about 100 pig/kg body weight/day, 10 pig/kg body weight/day to about 1 mg/kg body weight/day, 100 µg/kg body weight/day to about 10 mg/kg body weight/day, 1 mg/kg body weight/day to about 100 mg/kg body weight/day and 10 mg/kg body weight/day to about 100 mg/kg body weight/day.

In another embodiment, the antibody, or antigen-binding fragment thereof, is administered at a dosage range of 1 ng-10 ng per injection, 10 ng to 100 ng per injection, 100 ng to 1 µg per injection, 1 µg to 10 µg per injection, 10 µg to 100 µg per injection, 100 µg to 1 mg per injection, 1 mg to 10 mg per injection, 10 mg to 100 mg per injection, and 100 mg to 1000 mg per injection.

In another particular embodiment, the dose range of antibody, or antigen-binding fragment thereof, administered is from about 1 ng/kg to about 100 mg/kg In still another particular embodiment, the range of antibody administered is from about 1 ng/kg to about 10 ng/kg, about 10 ng/kg to about 100 ng/kg, about 100 ng/kg to about 1 µg/kg, about 1 µg/kg to about 10 µg/kg, about 10 µg/kg to about 100 µg/kg, about 100 µg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the amount of antibody, or antigen-binding fragment thereof, administered is, or is about, 0.0006, 0.001, 0.003, 0.006, 0.01, 0.03, 0.06, 0.1, 0.3, 0.6, 1, 3, 6, 10, 30, 60, 100, 300, 600 and 1000 mg/day. As expected, the dosage will be dependent on the condition, size, age and condition of the patient.

The antibody, or antigen-binding fragment thereof, may be administered, as appropriate or indicated, a single dose as a bolus or by continuous infusion, or as multiple doses by bolus or by continuous infusion. Multiple doses may be administered, for example, multiple times per day, once daily, every 2, 3, 4, 5, 6 or 7 days, weekly, every 2, 3, 4, 5 or 6 weeks or monthly. However, other dosage regimens may be useful. The progress of this therapy is easily monitored by conventional techniques.

The present invention is further illustrated by the following examples which should not be construed as limiting. The contents of all references, patents and published patent applications cited throughout this application, as well as the Figures and Tables, are incorporated herein by reference.

Example 1: 2A2 Ab Humanization and Production

Cloning of Variable Light and Heavy Chain of 2A2 from Hybridoma

2A2 hybridoma cells were harvested by centrifugation and total RNA was extracted from cells using RNA purification kit. This total RNA was used for cDNA synthesis and finally V-region genes of 2A2 were isolated using primer sets published in "Phage display manual". FIG. 1A shows the variable heavy (VH) and light chain sequences (VL) of 2A2.

Humanization of 2A2 Variable Region

Usually, rodent antibodies can be immunogenic to human and cause very serious side effects including the HAMA (human anti-mouse antibodies) response or anaphylactic shock. To overcome this problem, antibody engineering has been used to humanize non-human antibodies. Therefore, the CDR grafting method was used to humanize the VL and VH of 2A2.

CDR grafting is currently the most frequently used strategy for the humanization of rodent mAbs. In this approach, CDR loops that make up the antigen-binding site of the rodent mAb are grafted into the corresponding human framework regions.

To identify human VL and VH homologous to those of 2A2, the variable regions of 2A2 were compared with variable regions of human germline sequences using the VBASE online database (vbase.mrc-cpe.cam.ac.uk). As a result, two human germline VL and VH sequences were found. Amino acid sequence alignment of 2A2 clones and human germline sequence is shown in FIG. 1B.

The selected 2A2 VH sequence was found to be most homologous to the human V gene 1-46 from the VH1 family and human J gene JH6. The selected 2A2 VL sequence was found to be most homologous with the human V gene A1 from the Vk2 family and human J gene Jk2. So, synthesized VL and VH that each contained three of mouse CDR sequences were grafted into the selected human framework sequences for humanization of 2A2 mAb.

Vector Construction for the Expression of Humanized 2A2 IgG1 in Mammalian Cells

2A2 mAb is originally murine IgM. IgM antibodies are converted to the IgG1 format because IgG1 is the most abundant in serum (9 mg/ml), its half-life (21 days) is longer than any other antibodies, and, currently, most commercial therapeutic antibodies are IgG1 format. To construct humanized 2A2 IgG1 in a mammalian expression vector, pOptiVEC and pcDNA 3.3 (Invitrogen) vectors were used.

Vector for the Expression of Humanized 2A2 IgG1 in Mammalian Cells

The exemplary vector contains the human cytomegalovirus (CMV) immediate-early promoter/enhancer for high-level expression of recombinant proteins in a wide range of mammalian cells. To construction of humanized 2A2 IgG1, human variable light and heavy chain each with three CDRs of mouse 2A2 were synthesized and these two DNA fragments were linked to the human constant light and heavy chain by PCR. Finally, the humanized 2A2 light chain was cloned into pcDNA3.3 TOPO, and humanized 2A2 heavy chain was cloned into the pOptiVEC TOPO antibody expression vector. Sequences of human 2A2 IgG1 are shown in FIGS. 2A-B, which indicated that first amino acid (Arginine, red color shading) of human constant light chain was missed during construction of whole humanized light chain. After construction of these human 2A2 Ab expression vectors, the DNA plasmids were co-transfected into CHO-derived, DHFR-negative DG44 cells to create a stable cell line that produces 2A2 hIgG1 antibody.

Development of Stable Cell Lines for Antibody Production

To obtain cell lines that produce high levels of antibody, a pool of stably-transfected cells were selected by performing two rounds of selection using CD OptiCHO medium and CD OptiCHO medium with 500 µg/ml of Geneticine, followed by MTX genomic amplification selection and two rounds of single cell clonal selection in semi-solid media in a 96-well plate. Antibody expression levels were screened by ELISA assay quantification and selected h2A2IgG1-CHO cell (G3A10, C5G6 and D5F11) lines were slowly scaled up.

Example 2: Generation of Additional Anti-Ceramide Antibodies

A panel of monoclonal antibodies was generated for use in repeat-administration studies in mice to study immunogenicity. Screening of hybridomas to select anti-ceramide Mabs was performed by ELISA, using the antigen (Omega-COOH C16-ceramide coupled to albumin). Positive hits were counterscreened against both BSA and Omega-COOH C16-dihydroceramide coupled to albumin. Biologic testing of Mabs (in vitro inhibition of Jurkat cell apoptosis, in vivo inhibition of Radiation GI Syndrome) was then performed. Clones designated 9H10, 9H11, 9A2, 7B10, 6B5 and 6C8 were selected for testing and all but 9A2 demonstrated biologic activity in vitro. As shown in Table 1, a panel of clones preferentially bind C16:0 carboxyceramide-BSA. Ag1 is C16:0 carboxyceramide-BSA coated @ 300 ng/well, Ag2 is C-16:0 dihydro-carboxyceramide-BSA coated @ 300 ng/well and Ag3 is Free BSA (Sigma A6003) coated @ 300 ng/well.

TABLE 1

Anti-Ceramide mAbs

| Clone # | Ag1 OD (IgG(gamma)) | AG1 OD (IgM(Mµ)) | Ag2 OD (gamma) | Ag3 OD (gamma) |
|---|---|---|---|---|
| 6B5 | 2.201 | 0.054 | 0.049 | 1.295 |
| 7E8 | 1.530 | 0.045 | 0.077 | 0.906 |
| 8H8 | 3.000 | 0.103 | 0.098 | 3.000 |
| 9A2 | 3.000 | 0.055 | 0.078 | 3.000 |
| 7B10 | 0.080 | 0.180 | 0.078 | 0.077 |
| 9H10 | 0.052 | 0.230 | 0.064 | 0.095 |

TABLE 1-continued

Anti-Ceramide mAbs

| Clone # | Ag1 OD (IgG(gamma)) | AG1 OD (IgM(Mµ)) | Ag2 OD (gamma) | Ag3 OD (gamma) |
|---|---|---|---|---|
| 9H11 | 0.045 | 0.343 | 0.047 | 0.105 |
| 6C8 | 0.192 | 0.039 | 0.049 | 0.098 |
| NC | 0.047 | 0.066 | 0.048 | 0.096 |
| PC | 3.000 | 0.067 | 0.070 | 3.000 |

NC = 50% of culture media + 50% of 5% milk/PBS
PC = Cardiac Serum Mouse #1 @ 1:1K Clones 6B5 and 6C8 were identified as IgG while clones 7B10, 9H10 and 9H11 were identified as IgM. Additional data for those identified as IgG is found in Table 2. Ag1 is C16:0 carboxyceramide-BSA coated @ 500 ng/well in sodium bicarbonate, Ag2 is C-16:0 dihydro-carboxyceramide-BSA coated @ 500 ng/well in sodium bicarbonate and Ag3 is Free BSA (Sigma A6003) coated @ 500 ng/well in sodium bicarbonate.

TABLE 2

Concentration Curve of Anti-Ceramide mAbs

| Clone #/ Ab dilution | Ag1 (gamma) | AG1 (Mµ) | Ag2 (gamma) | Ag2 (Mµ) | Ag3 (gamma) | Ag3 (Mµ) |
|---|---|---|---|---|---|---|
| 6B5 (0.99 mg/ml) 10 µg/ml | 0.639 | | 0.072 | | 0.150 | |
| 6B5 (0.99 mg/ml) 1 µg/ml | 0.399 | | 0.089 | | 0.119 | |
| 6B5 (0.99 mg/ml) 0.1 µg/ml | 0.147 | | 0.072 | | 0.079 | |
| 6C8 (0.79 mg/ml) 10 µg/ml | 0.119 | | 0.073 | | 0.062 | |
| 6C8 (0.79 mg/ml) 1 µg/ml | 0.057 | | 0.074 | | 0.057 | |
| 6C8 (0.79 mg/ml) 0.1 µg/ml | 0.052 | | 0.068 | | 0.056 | |
| NC | 0.053 | 0.062 | 0.048 | 0.052 | 0.060 | 0.056 |
| PC | 1.426 | 0.218 | 0.094 | 0.070 | 0.350 | 0.127 |

NC = 5% milk-PBS
PC = CERM01 Tail Bleed Serum Mouse #1 @ 1:1K

FIG. 3 shows that clones 9H10, 9H11, 7B10, 6B5 and 6C8 demonstrate biologic activity in vitro.

Figure 4:
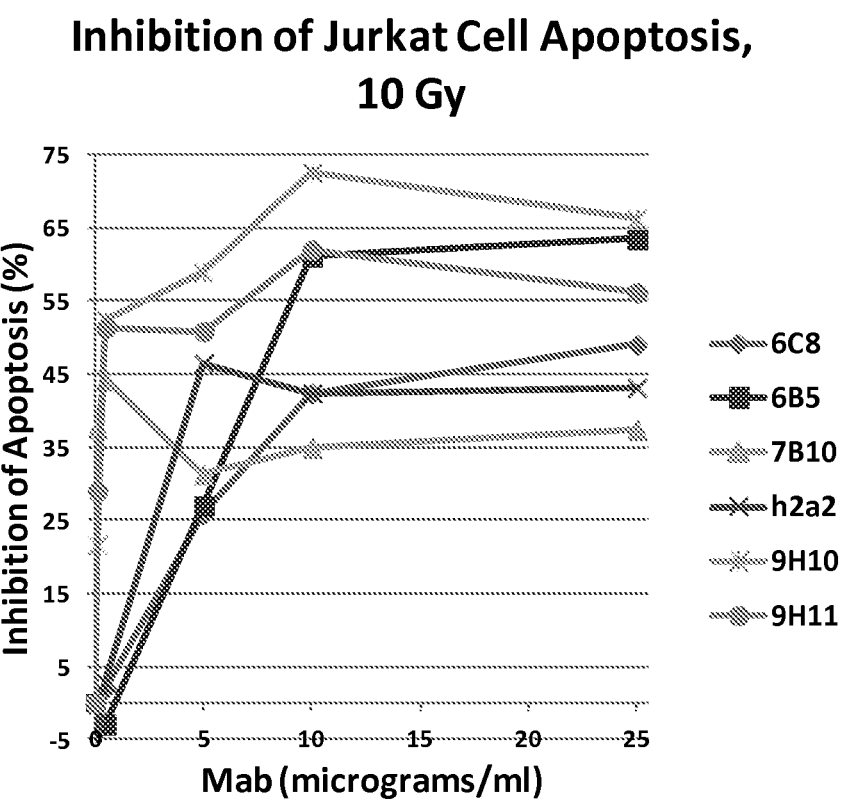
FIG. 4 is an illustration of an exemplary inhibition with purified antibody of Jurkat cell apoptosis, 10 Gy.

Positive clones were screened for biologic activity by exposing Jurkat cells to 10 Gy penetrating radiation. Monoclonal antibodies (Mabs) added to culture medium at indicated doses just prior to IR and the cells were fixed after 16 hr incubation. Apoptosis was quantified by HOESCHST bisbenzimide stain and morphologic examination. The results are shown in FIG. 4.

Figure 5:
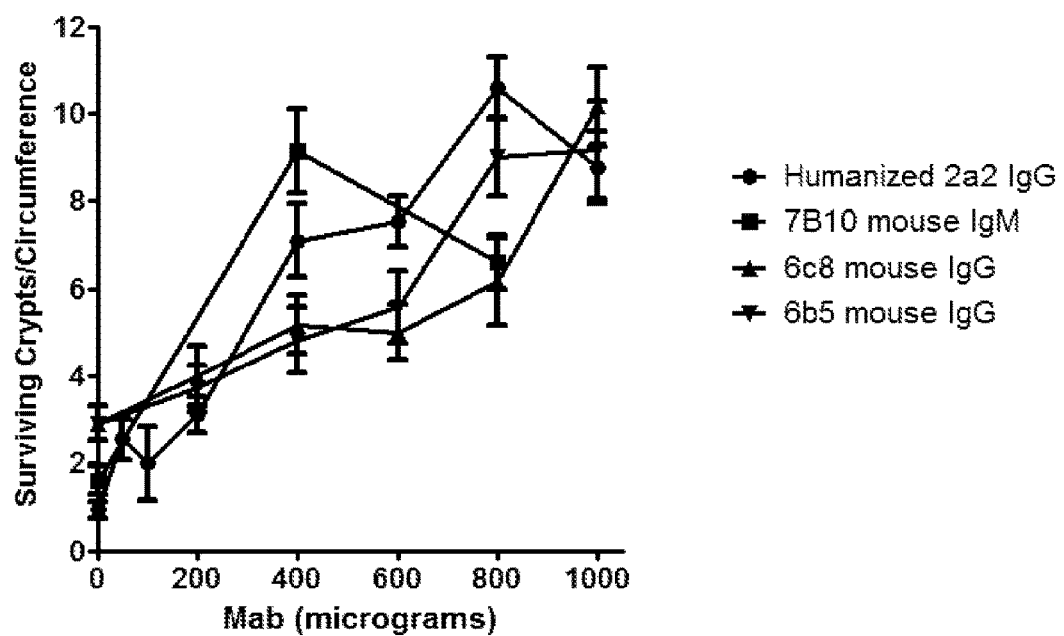
FIG. 5 is an illustration of an exemplary inhibition of crypt lethality using humanized 2a2 and murine 7B10, 6c8 and 6b5.

Crypt lethality was studied on clones 7B10 (IgM), 6B5 (IgG), and 6C8 (IgG). FIG. 5 shows that all dose-dependently inhibited crypt lethality when administered 15 minutes prior to the 15 Gy IR.

Figure 6:
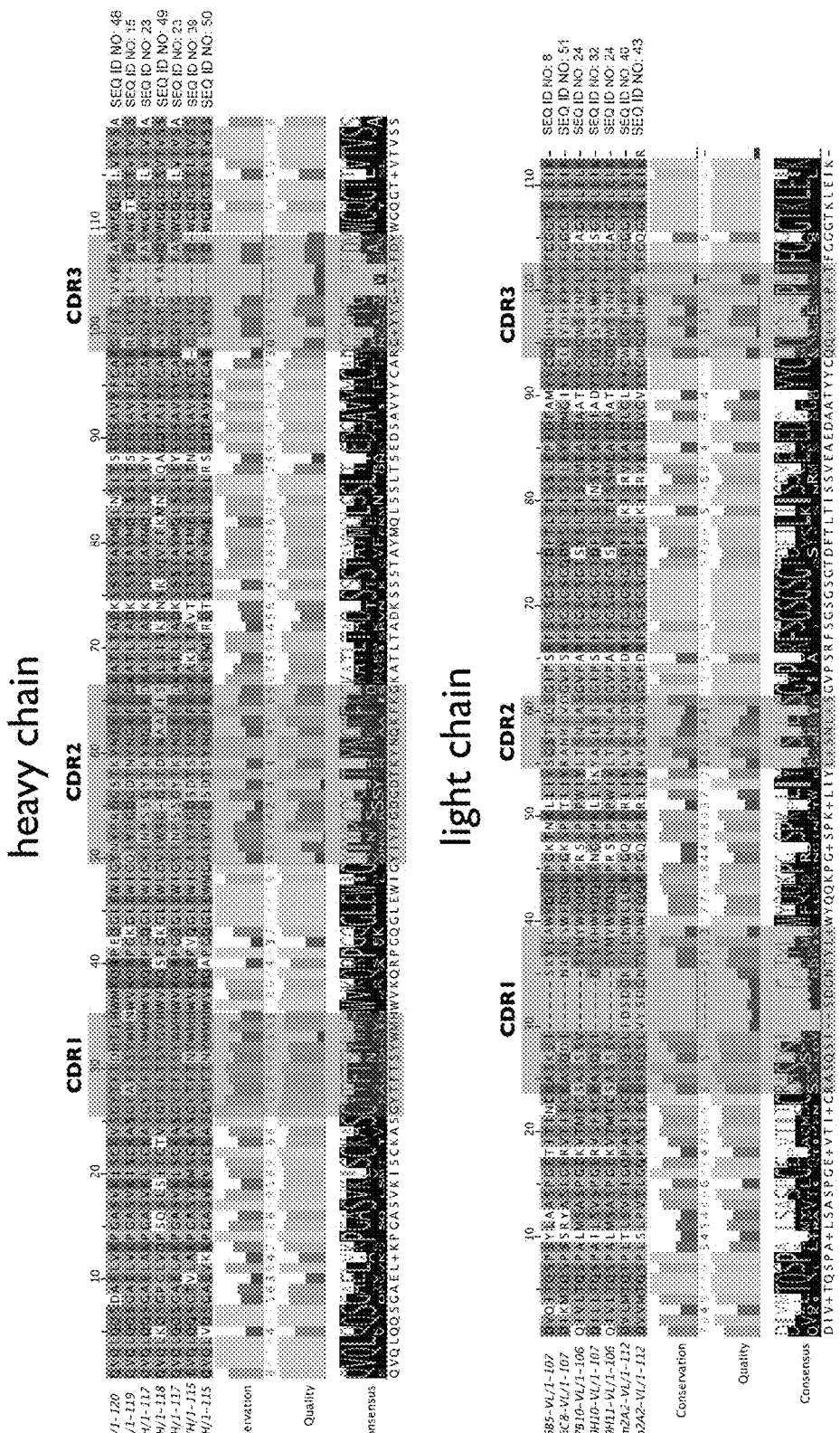
FIG. 6 is an illustration of exemplary sequences of mouse antibodies 6B5 (SEQ ID NOS 48 and 8, respectively, in order of appearance), 6C8 (SEQ ID NOS 15 and 51, respectively, in order of appearance), 7B10 (SEQ ID NOS 23-24, respectively, in order of appearance), 9H10 (SEQ ID NOS 49 and 32, respectively, in order of appearance), 9H11 (SEQ ID NOS 23-24, respectively, in order of appearance), 2A2 (SEQ ID NOS 39-40, respectively, in order of appearance) and humanized 2A2 antibody (h2A2) (SEQ ID NOS 50 and 43, respectively, in order of appearance), as well as depiction of an anti-ceramide consensus sequence. The alignment and consensus sequence are generated using the computer program MUSCLE multiple sequence alignment. Conservation is visualised on the alignment or a sequence group as a histogram giving the score for each column. Conserved columns are indicated by "*" (score of 11 with default amino acid property grouping), and columns with mutations where all properties are conserved are marked with a "+" (score of 10, indicating all properties are conserved). "−" means a gap.

The CDRs of 6B5, 6C8, 7B10, 9H10 and 9H11 were sequenced. Sequence data revealed significant homology amongst these Mabs, as well as with the CDRs of 2A2 (generated via an alternative immunization/screening protocol). IgMs appear to have even greater homology amongst each other and 2A2. In the same way the two IgG are most similar to each other. FIG. 6 shows a sequence alignment of the six murine antibody heavy and light chain variable region sequences, as well as the sequence for humanized h2A2 (derived from m2A2), as well as a depiction of a computer generated consensus sequence. In CDR1 of the heavy chain variable region, each of the antibodies comprise 10 amino acids comprising a Gly in the 1st position from the N-terminal, a Tyr or Phe in the 2nd position from the N-terminal, a Phe or Leu in the 4th position from the N-terminal, and a Thr or Ser in the 5th position from the N-terminal and a His or Asn in the 10th position from the N-terminal. In CDR2 of the heavy chain variable region, each of the antibodies comprise 16-17 amino acids comprising a Asn or Ile in the 2nd position from the N-terminal, a Phe or Ser in the 4th position from the N-terminal, a Thr in the 9th position from the C-terminal, a Tyr in the 7th position from the C-terminal, an Asn or Arg in the 6th position from the C-terminal, a Lys or Ala in the 4th position from the C-terminal and a Phe in the 3rd position from the C-terminal. In CDR3 of the heavy chain variable region of the murine antibodies, each of the antibodies comprise 7 to 11 amino acids comprising a Tyr or Thr at the 4th position from the N-terminal. In CDR1 of the light chain variable region, each of the antibodies comprise 10-16 amino acids comprising an Ala or Ser in the 2nd position from the N-terminal, a Ser in the 3rd position from the N-terminal, a Ser or Asp in the 5th position from the N-terminal, and a Tyr, Ser or Phe in the 3rd position from the C-terminal. In CDR2 of the light chain variable region, each of the antibodies comprise 7 amino acids comprising a Ser or Asn in the 3rd position from the N-terminal, a Lys or Ser in the 5th position from the N-terminal and a Ser or Asp in the 7th position from the N-terminal. In CDR3 of the light chain variable region, each of the murine antibodies comprise 9 amino acids comprising a Gln, Leu or Trp in the 1st position from the N-terminal, a Gln in the 2nd position from the N-terminal, a Pro in the 7th position from the N-terminal and a Thr in the 9th position from the N-terminal.

Also shown in FIG. 6 are anti-ceramide consensus sequence heavy chain and light chain CDRs based upon the sequence information derived from the CDR sequences of 6B5, 6C8, 7B10, 9H10 and 9H11. The present inventors have surprisingly found that the CDR regions of the light and heavy chain variable regions of the anti-ceramide antibodies have certain conserved amino acid residues. In some embodiments, a consensus sequence determined from the sequence of two or more of the anti-ceramide antibodies 6B5, 6C8, 7B10, 9H10, 9H11 and 2A2 can be used to generate an scFv antibody comprising consensus CDRs, consensus variable regions, or variable regions comprising at least about 80%, 90% or 95% sequence identity with a consensus variable region sequence.

Example 3: Generation of Anti-Ceramide scFv

Figure 7:
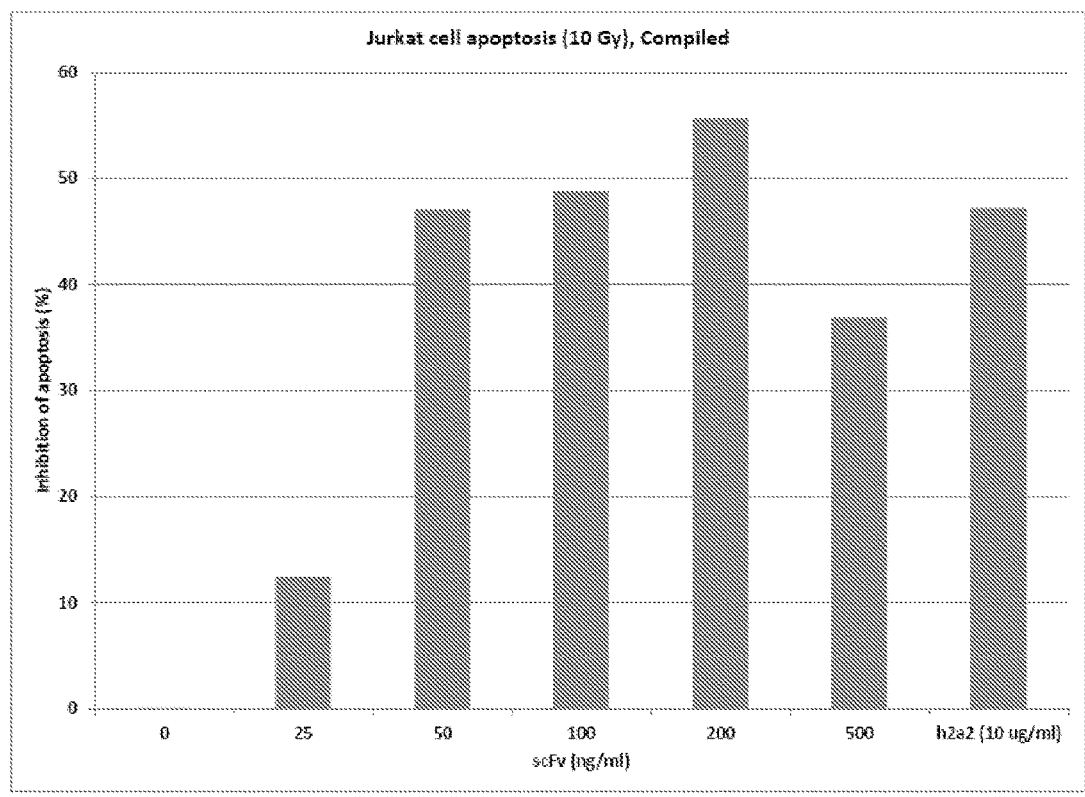
FIG. 7 is an illustration of an exemplary 6B5 scFv inhibition of Jurkat cell apoptosis in vitro.
Figure 8:
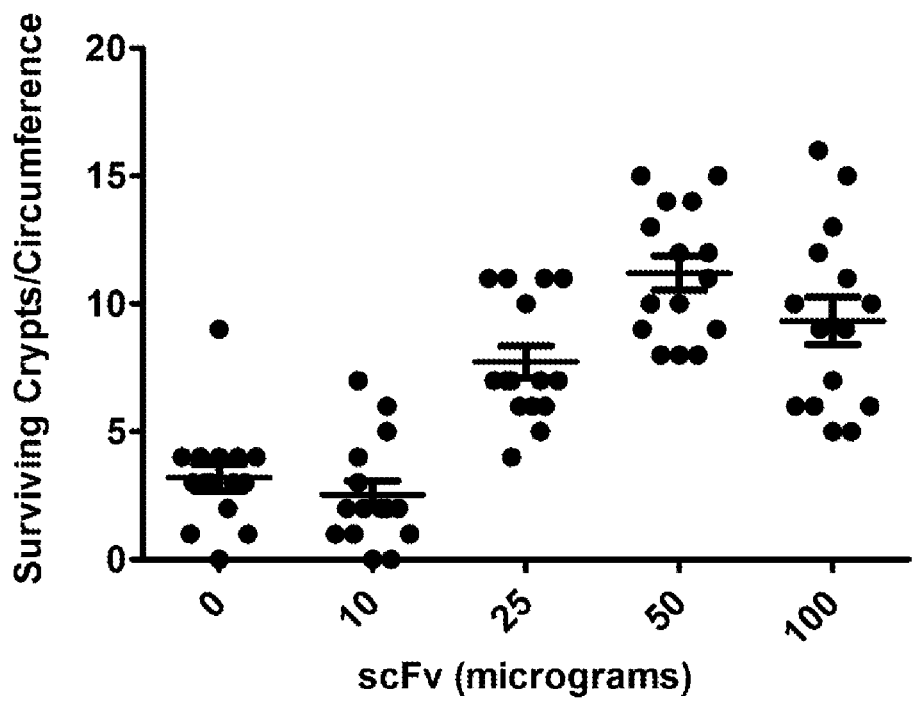
FIG. 8 is an illustration of an exemplary 6B5 scFv protection against GI crypt depletion in vivo when administered prior to exposure.
Figure 9:
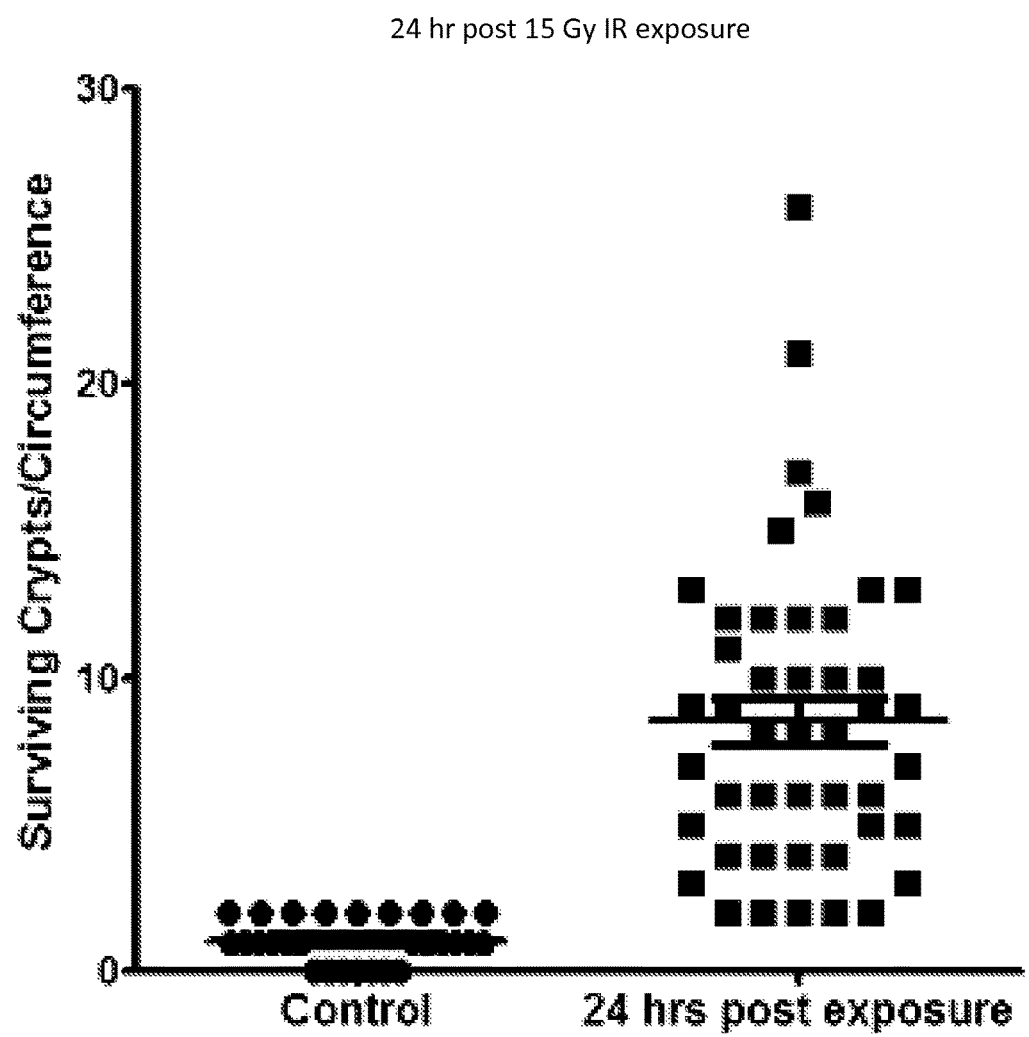
FIG. 9 is an illustration of an exemplary 6B5 scFv mitigation against GI crypt depletion in vivo when administered after exposure.

Based on Mab efficacy data, the CDRs of 6B5 were chosen (along with 2a2) to be engineered into a single-chain Fv. Two single chain (sc) Fv constructs were engineered to express the scFv and provide purified scFv for efficacy testing. 6B5 scFv was readily expressed and purified. Biologic testing of scFv, as with Mabs, was performed using in vitro inhibition of Jurkat cell apoptosis and in vivo inhibition of Radiation GI Syndrome. FIG. 5 shows that 6B5 IgG protects against crypt death via the microcolony assay. FIG. 7 shows scFv inhibits jurkat cell apoptosis. FIG. 8 shows that 6B5 scFv protects against GI crypt depletion in vivo when administered 15 minutes prior to 15 Gy exposure. FIG. 9 shows that 6B5 scFv mitigates against GI crypt depletion in vivo when administered 24 hours after 15 Gy exposure.
Anti-Ceramide scFv Protects Mice from Lethal Acute Graft-Versus-Host Disease C57BL/6 mice (MHC $H2^b$ haplotype) were administered saline, 50 mg/kg humanized anti-ceramide h2A2 or 7.5 mg/kg anti-ceramide scFv 6B5 via the indicated route of administration and dosing schedule. Dosing began 15 min prior to 1100 cGy split-dose total-body irradiation (TBI). Mice subsequently received an allogeneic bone marrow transplantation 16-20 hours post TBI consisting of $5\times10^6$ allogeneic bone marrow (BM) or BM and $2\times10^6$ allogeneic CD5+ naïve T cells from B10.BR donor mice (MHC $H2^{k2}$ haplotype). Mice were monitored daily for survival. Data represents Day 10 survival, determined to be representative of 90 day survival. An intravenous route of administration with saline on a dosing schedule of 0, 4, and 8 days resulted in 30% survival after 10 days. An intravenous route of administration with h2A2 monoclonal antibody on a dosing schedule of 0, 4, and 8 days resulted in 100% survival after 10 days (p<0.001 vs. saline control). An intravenous route of administration with scFv on a dosing schedule of 0, 4, and 8 days resulted in 60% survival after 10 days (p<0.05 vs. saline control). A subcutaneous route of administration with saline on a dosing schedule of 0, 2, 4, 6 and 8 days resulted in 0% survival after 10 days. A subcutaneous route of administration with saline on a dosing schedule of 0, 2, 4, 6 and 8 days resulted in 100% survival after 10 days (p<0.001 vs. saline control).

Figure 10:
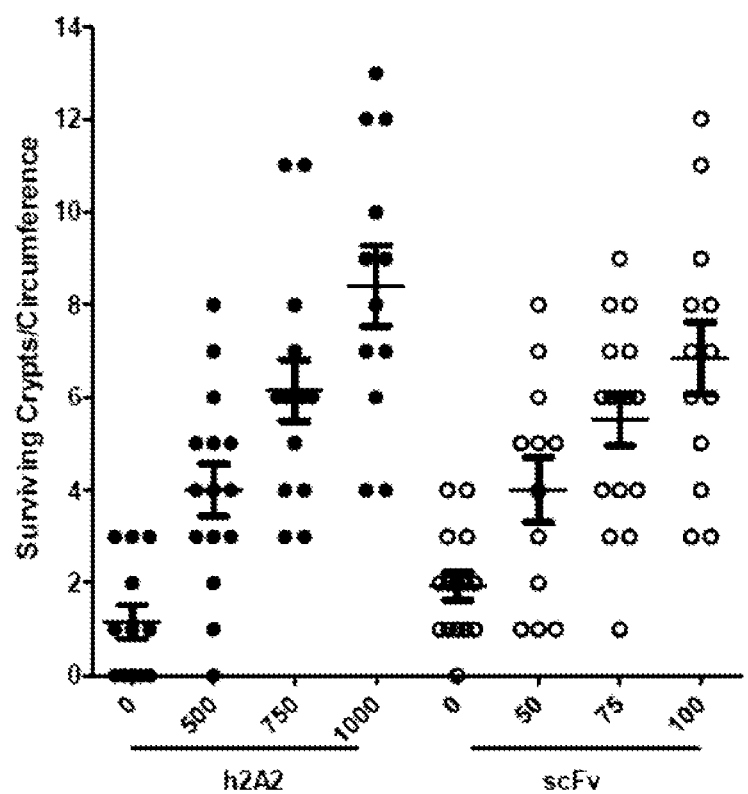
FIG. 10 is an illustration that anti-ceramide scFv protects intestinal crypts in a dose-dependent manner. C57BL/6 mice were administered humanized anti-ceramide 2A2 (0-1000 micrograms/mouse) or recombinant anti-ceramide scFv 6B5 (0-100 micrograms per mouse) via intravenous injection 15 min prior to 15 Gy total-body irradiation (TBI). Mice were euthanized 3.5 days following TBI, and a section of proximal jejunum was removed, cut into 3 15 mm segments, and placed in 4% paraformaldehyde. Proximal jejunum segments were cross-sectioned, mounted and slides were H&E stained prior to quantification of surviving crypts according to the method of Withers and Elkind (1970). As the intestinal crypt is the site of the intestinal stem cell, the microcolony assay is commonly used as a surrogate for intestinal stem cell survival. N=5 mice per group.
Figure 11:
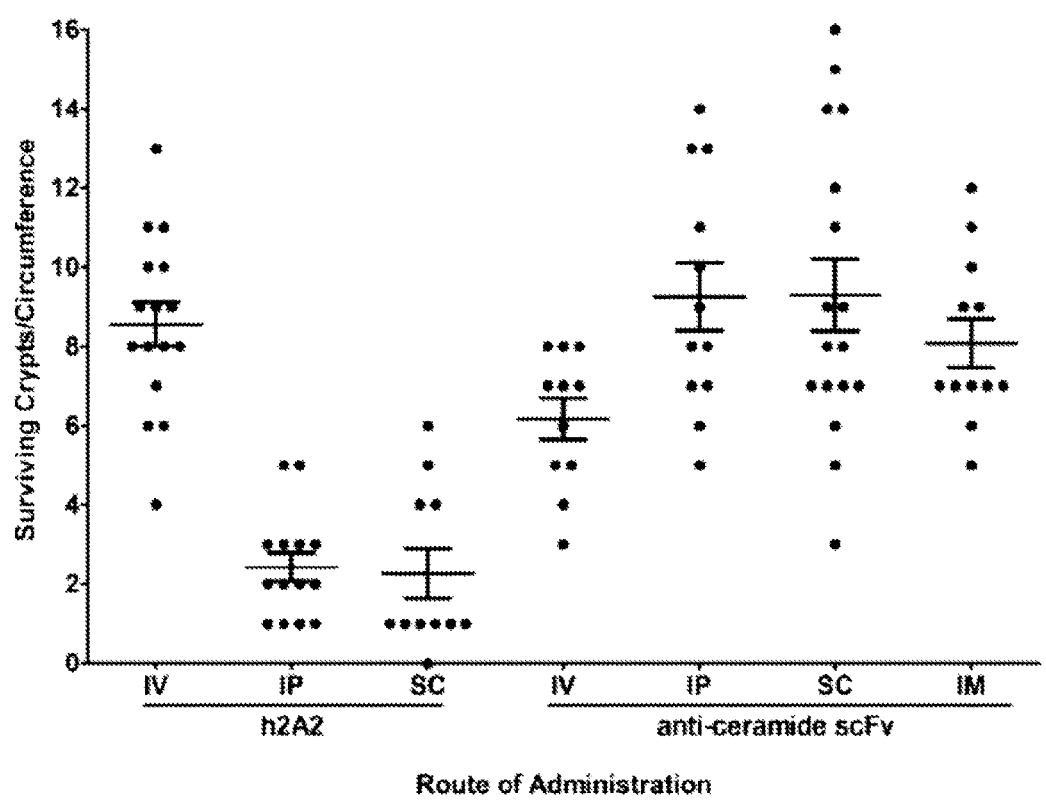
FIG. 11 is an illustration that anti-ceramide scFv retains efficacy when administered via alternative injections. C57BL/6 mice were administered humanized 2A2 anti-ceramide antibody (50 mg/kg) via intravenous (IV), intraperitoneal (IP) or subcutaneous (SC) injection 15 min prior to exposure to 15 Gy total-body irradiation. Alternatively, mice were administered 7.5 mg/kg anti-ceramide scFv 6B5 via IV, IP, SC or intramuscular (IM) injection 15 min prior to 15 Gy total-body irradiation (TBI). Mice were euthanized 3.5 days following TBI, and a section of proximal jejunum was removed, cut into 3 15 mm segments, and placed in 4% paraformaldehyde. Proximal jejunum segments were cross-sectioned, mounted and slides were H&E stained prior to quantification of surviving crypts according to the method of Withers and Elkind (1970). As the intestinal crypt is the site of the intestinal stem cell, the microcolony assay is commonly used as a surrogate for intestinal stem cell survival. N=5 mice per group.
Figure 12:
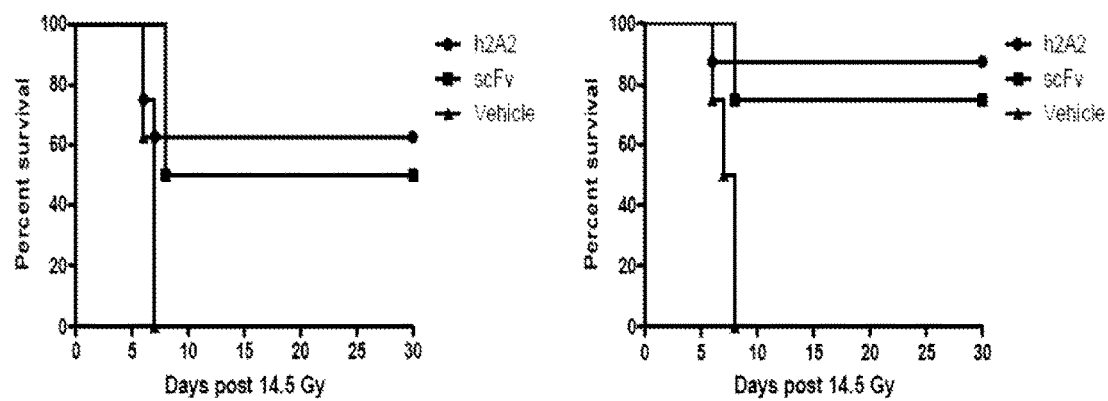
FIG. 12 is an illustration that anti-ceramide h2a2 and scFv protect and mitigate the lethal effects of Radiation GI Syndrome. (left panel) C57BL/6 mice were administered humanized anti-ceramide 2A2 (1000 micrograms/mouse) via intravenous injection or recombinant anti-ceramide scFv 6B5 (100 micrograms per mouse) via subcutaneous injection 15 min prior to 14.5 Gy total-body irradiation (TBI). Mice received 5×106 autologous bone marrow cells 16 hours post TBI and were monitored daily for morbidity and mortality. Mice considered moribund were euthanized immediately. Data represents a Kaplan-Meier survival plot analyzed by Log-rank test. P<0.05 for both h2A2 and scFv groups vs. saline control. (right panel). Experiment was performed exactly as in left panel, except humanized anti-ceramide 2A2 (1000 micrograms/mouse) via intravenous injection or recombinant anti-ceramide scFv 6B5 (100 micrograms per mouse) via subcutaneous injection were administered 24 hours post 14.5 Gy total-body irradiation (TBI). N=5 mice per group. P<0.05 for both h2A2 and scFv groups vs. saline control.
Figure 13:
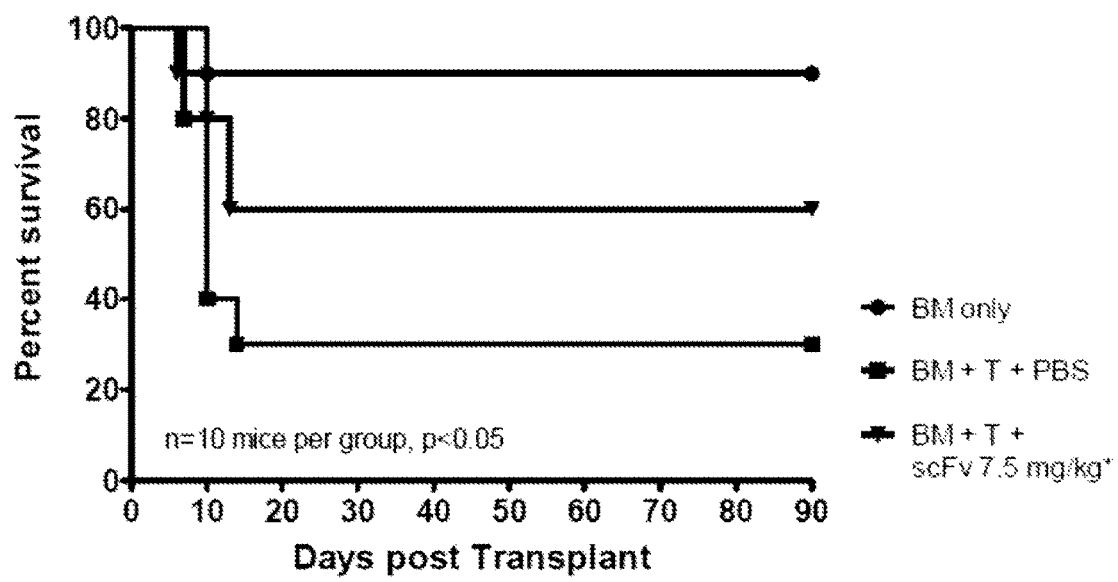
FIG. 13 is an illustration that anti-ceramide scFv protects mice from lethal acute graft-versus-host disease. C57BL/6 mice (MHC $H2^b$ haplotype) were administered PBS or 7.5 mg/kg anti-ceramide scFv 6B5 via intravenous injection 15 min prior to 1100 cGy split-dose total-body irradiation (TBI). Mice received an allogeneic bone marrow transplantation 16-20 hours post TBI consisting of 5×10⁶ bone marrow (BM) or BM and 2×10⁶ CD5+ naïve T cells from B10.BR donor mice (MHC H2' haplotype). Mice received PBS or 7.5 mg/kg anti-ceramide scFv 6B5 on days 4, 8, 12 and 16. Mice were scored weekly for GvHD-associated morbidity, including weight loss, skin lesions, fur ruffling and loss and kyphosis, and monitored for survival. Data represents a Kaplan-Meier survival plot analyzed by Log-rank test. P<0.05 for scFv group vs. saline control.
Figure 14:
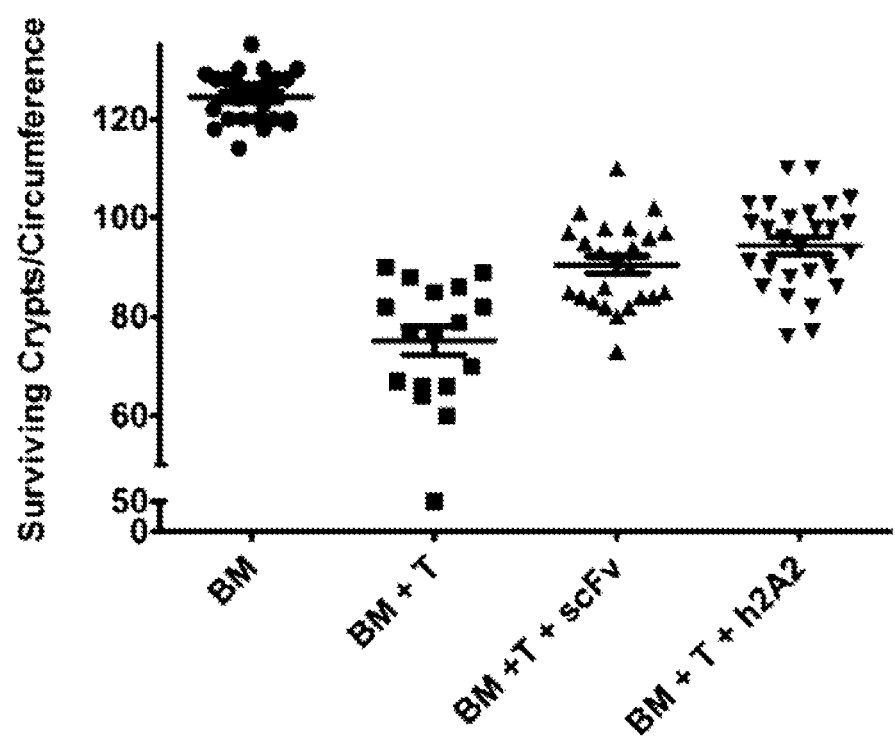
FIG. 14 is an illustration that anti-ceramide scFv protects mouse intestinal stem cells during lethal acute graft-versus-host disease. C57BL/6 mice (MHC $H2^b$ haplotype) were administered PBS, 50 mg/kg humanized h2A2 antibody or 7.5 mg/kg anti-ceramide scFv 6B5 via intravenous injection 15 min prior to 1100 cGy split-dose total-body irradiation (TBI). Mice received an allogeneic bone marrow transplantation 16-20 hours post TBI consisting of 5×106 bone marrow (BM) or BM and 2×10⁶ CD5+ naïve T cells from B10.BR donor mice (MHC $H2^{k2}$ haplotype). Mice received PBS or 7.5 mg/kg anti-ceramide scFv 6B5 on days 4 and 8. Mice were euthanized day 10 post transplant, and a section of proximal jejunum was removed, cut into 3 15 mm segments, and placed in 4% paraformaldehyde. Proximal jejunum segments were cross-sectioned, mounted and slides were H&E stained prior to quantification of surviving crypts according to the method of Withers and Elkind (1970). As the intestinal crypt is the site of the intestinal stem cell, the microcolony assay is commonly used as a surrogate for intestinal stem cell survival. N=5 mice per group.
Figure 15:
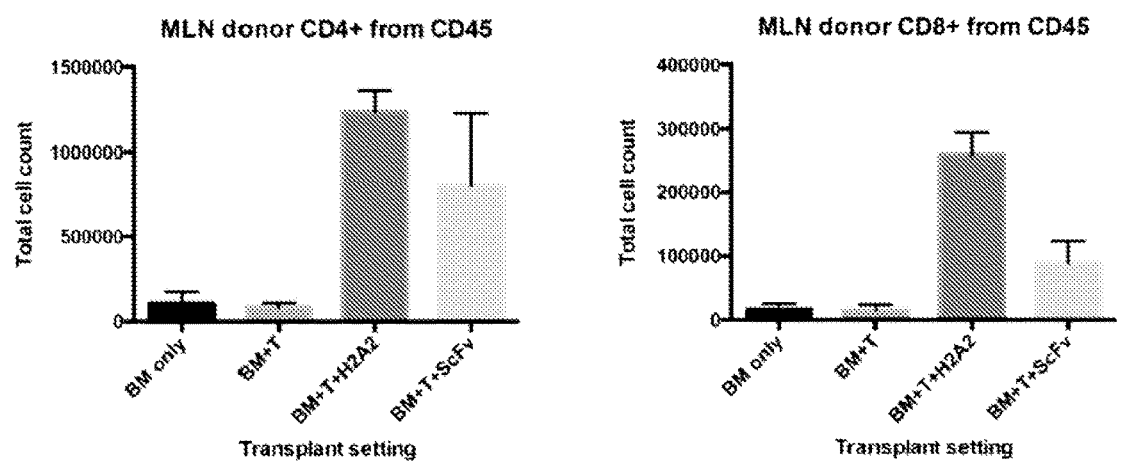
FIG. 15 is an illustration that anti-ceramide h2A2 and scFv increase retention of CD4+ and CD8+ lymphocytes within the mesentery lymph nodes. C57BL/6 mice (MHC $H2^b$ haplotype) were administered PBS, 50 mg/kg humanized h2A2 antibody or 7.5 mg/kg anti-ceramide scFv 6B5 via intravenous injection 15 min prior to 1100 cGy split-dose total-body irradiation (TBI). Mice received an allogeneic bone marrow transplantation 16-20 hours post TBI consisting of 5×10⁶ bone marrow (BM only) or BM and 2×10⁶ CD5+ naïve T cells from B10.BR donor mice (MHC H2k2 haplotype). Mice subsequently received PBS, h2A2 or scFv 6B5 on days 4 and 8. Mice were euthanized day 10 post transplant, and mesentery lymph nodes wee analyzed by flow cytometry. Data represents the total number of CD4+ and CD8+ cells from the total donor ($H2^{k2}$ haplotype positive) CD45+ lymphocyte pool. N=5 mice per group.

As shown in FIG. 10, anti-ceramide scFV protects intestinal crypts in a dose-dependent manner. As shown in FIG. 11, anti-ceramide scFv retains efficacy when administered via alternative injections. As shown in FIG. 12, anti-ceramide h2A2 and scFv protect and mitigate the lethal effects of Radiation GI Syndrome. As shown in FIG. 13, anti-ceramide scFv protects mice from lethal acute graft-versus-host disease. As shown in FIG. 14, anti-ceramide scFv protects mouse intestinal stem cells during lethal acute graft-versus-host disease. As shown in FIG. 15, anti-ceramide h2A2 and scFv increase retention of CD4+ and CD8+ lymphocytes within the mesentery lymph nodes (FIG. 15).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. An anti-ceramide antibody or antigen-binding fragment thereof comprising a variable heavy chain (VH) and a variable light chain (VL), wherein
   the VH comprises a heavy chain variable region CDR1 comprising the sequence GYTFTDHTIH (SEQ ID NO: 1), a heavy chain variable region CDR2 comprising the sequence YNYPRDGSTKYNEKFKG (SEQ ID NO: 2), and a heavy chain variable region CDR3 comprising the sequence GFITTVVPSAY (SEQ ID NO: 3), and
   the VL comprises a light chain variable region CDR1 comprising the sequence RASKSISKYLA (SEQ ID NO: 4), a light chain variable region CDR2 comprising the sequence SGSTLQS (SEQ ID NO: 5), and a light chain variable region CDR3 comprising the sequence QQHNEYPWT (SEQ ID NO: 6).

2. An anti-ceramide antibody or antigen-binding fragment thereof comprising
   a heavy chain variable region sequence of QVQLQQS-DAELVKPGASVKISCKVSGYTFTDHTIHWM-KQRPEQGLEWIGYNYPRDGSTKYNEKFKG-KATLTADKSSSTAYMQLNSLTSEDSAV YFCAKGF-ITTVVPSAYWGQGTLV TVSA (SEQ ID NO: 48); and
   a light chain variable region sequence of DVQITQSPSY-LAASPGETITINCRASKSISKYLAWYQEKPGK-TNKLLIYSGSTLQSGIPSRF SGSGSGTDFTLTISS LEPEDFAMYYCQQHNEYPWTFGGGTKLEIK (SEQ ID NO: 8).

3. The anti-ceramide antibody or antigen-binding fragment of claim 1, wherein the antibody is selected from the group consisting of a monoclonal antibody, a chimeric antibody, a humanized antibody, a human antibody and a scFv.

4. The anti-ceramide antibody of claim 3, wherein the antibody is a scFv.

* * * * *

SEQUENCE LISTING

<160> NUMBER OF SEQ ID NOS: 51

<210> SEQ ID NO 1
<211> LENGTH: 10
<212> TYPE: PRT
<213> ORGANISM: Artificial Sequence

```
<220> FEATURE:
<223> OTHER INFORMATION: Description of Artificial Sequence: Synthetic
      heavy chain variable region CDR1 of the anti-ceramide
      antibody

<400> SEQUENCE: 1

Gly Tyr Thr Phe Thr Asp His Thr Ile His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain variable region CDR2

<400> SEQUENCE: 2

Tyr Asn Tyr Pro Arg Asp Gly Ser Thr Lys Tyr Asn Glu Lys Phe Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      heavy chain variable region CDR3

<400> SEQUENCE: 3

Gly Phe Ile Thr Thr Val Val Pro Ser Ala Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR1

<400> SEQUENCE: 4

Arg Ala Ser Lys Ser Ile Ser Lys Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR2

<400> SEQUENCE: 5

Ser Gly Ser Thr Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR3

<400> SEQUENCE: 6
```

Gln Gln His Asn Glu Tyr Pro Trp Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      heavy chain variable region sequence

<400> SEQUENCE: 7

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
                20                  25                  30

Thr Ile His Trp Met Lys Gln Arg Pro Glu Gln Gly Leu Glu Trp Ile
            35                  40                  45

Gly Tyr Asn Pro Arg Asp Gly Ser Thr Lys Tyr Asn Glu Lys Phe Gly
        50                  55                  60

Lys Ala Thr Leu Thr Asp Ala Asp Lys Ser Ser Ser Thr Ala Tyr Met
65                  70                  75                  80

Gln Leu Asn Ser Leu Thr Ser Glu Asp Ser Ala Val Tyr Phe Cys Ala
                85                  90                  95

Lys Gly Phe Ile Thr Thr Val Val Pro Ser Ala Tyr Trp Gly Gln Gly
            100                 105                 110

Thr Leu Val Thr Val Ser Ala
        115

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable region sequence

<400> SEQUENCE: 8

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain variable region CDR1

```
<400> SEQUENCE: 9

Gly Tyr Ala Phe Ser Ser Tyr Trp Met Asn
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain variable region CDR2

<400> SEQUENCE: 10

Gln Ile Tyr Pro Gly Asp Gly Asp Thr Asn Tyr Asn Gly Lys Phe Lys
1               5                   10                  15

Gly

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain variable region CDR3

<400> SEQUENCE: 11

Arg Cys Tyr Tyr Gly Leu Tyr Phe Asp Val
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR1

<400> SEQUENCE: 12

Lys Ala Ser Gln Asp Ile Asn Arg Tyr Leu Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR2

<400> SEQUENCE: 13

Arg Ala Asn Arg Leu Val Asp
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR3

<400> SEQUENCE: 14

Leu Gln Tyr Asp Glu Phe Pro Tyr Thr
1               5

<210> SEQ ID NO 15
```

```
<211> LENGTH: 119
<212> TYPE: PRT
<213> ORGANISM: Artificial Sequence
<220> FEATURE:
<223> OTHER INFORMATION: Description of Artificial Sequence: Synthetic
      heavy chain variable region sequence

<400> SEQUENCE: 15

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Lys Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Arg Cys Tyr Tyr Gly Leu Tyr Phe Asp Val Trp Gly Thr Gly
                100                 105                 110

Thr Thr Val Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      light chain variable region sequence

<400> SEQUENCE: 16

Asp Ile Lys Met Thr Gln Ser Pro Ser Ser Arg Tyr Ala Ser Leu Gly
1               5                   10                  15

Glu Arg Val Thr Ile Thr Cys Lys Ala Ser Gln Asp Ile Asn Arg Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Ser Arg Phe Ser
        50                  55                  60

Gly Ser Gly Ser Gly Gln Asp Tyr Ser Leu Thr Ile Ser Ser Leu Glu
65                  70                  75                  80

Tyr Glu Asp Met Gly Ile Tyr Tyr Cys Leu Gln Tyr Asp Glu Phe Pro
                85                  90                  95

Tyr Thr Phe Gly Gly Gly Thr Lys Leu Glu Ile Lys
                100                 105

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain variable region CDR1 of the anti-ceramide
      antibody

<400> SEQUENCE: 17

Gly Tyr Thr Phe Thr Ser Tyr Trp Met His
1               5                   10
```

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain variable region CDR2

<400> SEQUENCE: 18

Tyr Ile Asn Pro Ser Ser Gly Tyr Thr Lys Tyr Asn Gln Phe Lys Asp
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      heavy chain variable region CDR3

<400> SEQUENCE: 19

Gly Gly Tyr Tyr Gly Phe Ala Tyr
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      light chain variable region CDR1

<400> SEQUENCE: 20

Ser Ala Ser Ser Ser Val Ser Tyr Met Tyr
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR2

<400> SEQUENCE: 21

Leu Thr Ser Asn Leu Ala Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR3

<400> SEQUENCE: 22

Gln Gln Trp Ser Ser Asn Pro Leu Thr
1               5

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      heavy chain variable region sequence

<400> SEQUENCE: 23

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Tyr Thr Lys Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Tyr Glu Asp Ser Ala Val Tyr Tyr Cys
                85                  90                  95

Ala Arg Gly Gly Tyr Tyr Gly Phe Ala Tyr Trp Gly Gln Gly Thr Leu
            100                 105                 110

Val Thr Val Ser Ala
        115

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      light chain variable region sequence

<400> SEQUENCE: 24

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain variable region CDR1 of the anti-ceramide
      antibody

<400> SEQUENCE: 25

Gly Phe Ser Leu Thr Gly Tyr Gly Val His
1               5                   10

<210> SEQ ID NO 26
<211> LENGTH: 16
<212> TYPE: PRT
<213> ORGANISM: Artificial Sequence

```
<220> FEATURE:
<223> OTHER INFORMATION: Description of Artificial Sequence: Synthetic
      heavy chain variable region CDR2

<400> SEQUENCE: 26

Val Ile Trp Ser Gly Gly Ser Thr Asp Tyr Asn Ala Ala Phe Ile Ser
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain variable region CDR3

<400> SEQUENCE: 27

Asn Tyr Gly Tyr Asp Tyr Ala Met Asp Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain variable region CDR1

<400> SEQUENCE: 28

Arg Ala Ser Gln Ser Ile Gly Thr Ser Ile His
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR2

<400> SEQUENCE: 29

Tyr Ala Ser Glu Ser Ile Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain variable region CDR3

<400> SEQUENCE: 30

Gln Gln Ser Asn Ser Trp Pro Phe Thr
1               5

<210> SEQ ID NO 31
<211> LENGTH: 116
<212> TYPE: PRT
<213> ORGANISM: Artificial Sequence
<220> FEATURE:
<223> OTHER INFORMATION: Description of Artificial Sequence: Synthetic
      heavy chain variable region sequence

<400> SEQUENCE: 31

Gln Val Gln Leu Lys Gln Ser Gly Pro Gly Val Gln Pro Ser Ser Leu
1               5                   10                  15
```

```
Ser Ile Thr Cys Thr Val Ser Gly Phe Ser Leu Ser Tyr Gly Val
            20                  25                  30

His Trp Val Arg Gln Ser Pro Gly Lys Gly Leu Glu Trp Leu Gly Val
        35                  40                  45

Ile Trp Ser Gly Gly Ser Thr Asp Tyr Asn Ala Ala Phe Ile Ser Arg
50                  55                  60

Leu Ser Ile Ser Lys Asp Asn Ser Lys Ser Gln Val Phe Phe Lys Met
65                  70                  75                  80

Asn Ser Leu Gln Ala Asp Asp Thr Ala Ile Tyr Tyr Cys Ala Arg Asn
                85                  90                  95

Tyr Gly Tyr Asp Tyr Ala Met Asp Tyr Trp Gly Gln Gly Thr Ser Val
            100                 105                 110

Thr Val Ser Ser
        115

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable region sequence

<400> SEQUENCE: 32

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Phe
                85                  90                  95

Thr Phe Gly Ser Gly Thr Lys Leu Glu Ile Lys
            100                 105

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain variable region CDR1 of the anti-ceramide
      antibody

<400> SEQUENCE: 33

Gly Tyr Thr Phe Thr Asn Tyr Trp Met His
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain variable region CDR2

<400> SEQUENCE: 34
```

```
Ala Ile Tyr Pro Gly Asp Ser Asp Thr Ser Tyr Asn Gln Lys Phe Lys
1               5                   10                  15

Gly
```

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain variable region CDR3

<400> SEQUENCE: 35

```
Gly Leu Tyr Tyr Gly Tyr Asp
1               5
```

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      light chain variable region CDR1

<400> SEQUENCE: 36

```
Lys Ser Ser Gln Ser Leu Ile Asp Ser Asp Gly Lys Thr Phe Leu Asn
1               5                   10                  15
```

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain variable region CDR2

<400> SEQUENCE: 37

```
Leu Val Ser Lys Leu Asp Ser
1               5
```

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      said light chain variable region CDR3

<400> SEQUENCE: 38

```
Trp Gln Gly Thr His Phe Pro Tyr Thr
1               5
```

<210> SEQ ID NO 39
<211> LENGTH: 115
<212> TYPE: PRT
<213> ORGANISM: Artificial Sequence
<220> FEATURE:
<223> OTHER INFORMATION: Description of Artificial Sequence: Synthetic
      heavy chain variable region sequence comprising  the
      sequence

<400> SEQUENCE: 39

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Asn Tyr
            20                  25                  30
```

Trp Met His Trp Val Lys Gln Arg Pro Val Gln Gly Leu Glu Trp Ile
            35                  40                  45

Gly Ala Ile Tyr Pro Gly Asp Ser Asp Thr Ser Tyr Asn Gln Lys Phe
 50                      55                  60

Lys Gly Lys Ala Lys Leu Thr Ala Val Thr Ser Thr Ser Thr Ala Phe
 65                  70                  75                  80

Met Glu Leu Ser Ser Leu Thr Asn Glu Asp Ser Ala Val Tyr Tyr Cys
                 85                  90                  95

Thr Gly Leu Tyr Tyr Gly Tyr Asp Trp Gly Gln Gly Thr Thr Leu Thr
            100                 105                 110

Val Ser Ser
        115

<210> SEQ ID NO 40
<211> LENGTH: 112
<212> TYPE: PRT
<213> ORGANISM: Artificial Sequence
<220> FEATURE:
<223> OTHER INFORMATION: Description of Artificial Sequence: Synthetic
      light chain variable region sequence

<400> SEQUENCE: 40

Asp Val Leu Met Thr Gln Thr Pro Leu Thr Leu Ser Val Thr Ile Gly
 1               5                  10                  15

Gln Pro Ala Ser Ile Ser Cys Lys Ser Ser Gln Ser Leu Ile Asp Ser
            20                  25                  30

Asp Gly Lys Thr Phe Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Leu Tyr Tyr Cys Trp Gln Gly
                 85                  90                  95

Thr His Phe Pro Tyr Thr Phe Gly Gly Gly Thr Lys Leu Glu Ile Lys
            100                 105                 110

<210> SEQ ID NO 41
<211> LENGTH: 109
<212> TYPE: PRT
<213> ORGANISM: Homo sapiens
<220> FEATURE:
<223> OTHER INFORMATION: Human V gene 1-46

<400> SEQUENCE: 41

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Trp Gly Gln Gly Thr Thr Val Thr Val Ser Ser

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      VL 2A2

<400> SEQUENCE: 42

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Ile Asp Ser
            20                  25                  30

Asp Gly Lys Thr Phe Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Leu Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg

<210> SEQ ID NO 43
<211> LENGTH: 112
<212> TYPE: PRT
<213> ORGANISM: Homo sapiens
<220> FEATURE:
<223> OTHER INFORMATION: Human V gene A1

<400> SEQUENCE: 43

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Thr Phe Gly Gln Gly Thr Lys Leu Glu Ile Lys Arg
            100                 105                 110

<210> SEQ ID NO 44
<211> LENGTH: 1395
<212> TYPE: DNA
<213> ORGANISM: Artificial Sequence
<220> FEATURE:
<223> OTHER INFORMATION: Description of Artificial Sequence: Synthetic
      Humanized 2A2 Heavy chain sequence

<400> SEQUENCE: 44
atggactgga cctggagggt cttctgcttg ctggctgtag ctccaggtgc tcactcccag      60

```
gtgcagcttg tgcagtctgg ggctgaggtg aaaaagcctg gggcttcagt gaaggtgtcc      120
tgcaaggctt ctggctacac ctttaccaac tactggatgc actgggtaag acaggcgcct      180
ggacagggtc tggaatggat gggcgctatt tatcctggag atagtgatac tagctacaac      240
cagaagttca agggccgggt cacaatgact cgagacacat ccaccagcac tgtctacatg      300
gagctcagca gcctgagaag tgaggacact gcggtctatt actgtgcacg cctttactac      360
ggctacgact gggccaaggc accactgtc acagtctcct cagccagcac gaagggccca      420
tcggtcttcc ccctggcacc ctcctccaag agcacctctg ggggcacagc ggccctgggc      480
tgcctggtca aggactactt ccccgaaccg gtgacggtgt cgtggaactc aggcgccctg      540
accagcggcg tgcacacctt cccggctgtc ctacagtcct caggactcta ctccctcagc      600
agcgtggtga ccgtgccctc cagcagcttg ggcacccaga cctacatctg caacgtgaat      660
cacaagccca gcaacaccaa ggtggacaag aaagttgagc ccaaatcttg tgacaaaact      720
cacacatgcc caccgtgccc agcacctgaa ctcctggggg gaccgtcagt cttcctcttc      780
cccccaaaac ccaaggacac cctcatgatc tcccggaccc ctgaggtcac atgcgtggtg      840
gtggacgtga gccacgaaga ccctgaggtc aagttcaact ggtacgtgga cggcgtggag      900
gtgcataatg ccaagacaaa gccgcgggag gagcagtaca acagcacgta ccgtgtggtc      960
agcgtcctca ccgtcctgca ccaggactgg ctgaatggca aggagtacaa gtgcaaggtc     1020
tccaacaaag ccctcccagc ccccatcgag aaaaccatct ccaaagccaa agggcagccc     1080
cgagaaccac aggtgtacac cctgccccca tcccgggatg agctgaccaa gaaccaggtc     1140
agcctgacct gcctggtcaa aggcttctat cccagcgaca tcgccgtgga gtgggagagc     1200
aatgggcagc cggagaacaa ctacaagacc acgcctcccg tgctggactc cgacggctcc     1260
ttcttcctct acagcaagct caccgtggac aagagcaggt ggcagcaggg gaacgtcttc     1320
tcatgctccg tgatgcatga ggctctgcac aaccactaca cgcagaagag cctctccctg     1380
tccccgggta aatga                                                       1395
```

<210> SEQ ID NO 45
<211> LENGTH: 463
<212> TYPE: PRT
<213> ORGANISM: Artificial Sequence
<220> FEATURE:
<223> OTHER INFORMATION: Description of Artificial Sequence: Synthetic Humanized 2A2 Heavy chain sequence

<400> SEQUENCE: 45

```
Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Met His Trp Val Arg Gln Ala Pro Gly Gln Gly Leu
    50                  55                  60

Glu Trp Met Gly Ala Ile Tyr Pro Gly Asp Ser Asp Thr Ser Tyr Asn
65                  70                  75                  80

Gln Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110
```

Tyr Tyr Cys Ala Arg Leu Tyr Gly Tyr Asp Trp Gly Gln Gly Thr
            115                 120                 125

Thr Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
    275                 280                 285

Glu Val Lys Phe Asn Trp Tyr Val Asp Gly Val Glu Val His Asn Ala
290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly
    450                 455                 460

<210> SEQ ID NO 46
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atgaggctcc ctgctcagct cctggggctg ctaatgctct gggtcccagg atccagtggg    60

```
gatgttgtga tgacccaatc tccactctct tgccggtta cccttggaca accagcctcc      120
atctcttgca agtcaagtca gagcctcata gatagtgatg aaagacatt tttgaattgg      180 ttccaacaga ggccaggcca gtctccaagg cgcctaatct atctggtgtc taaactggac    240
tctggagtcc ctgacaggtt ctctggcagt ggatcaggga cagatttcac tctgaaaatc    300
agcagagtgg aggctgagga tgtgggagtt tattattgct ggcaaggtac acattttccg    360
tacacgttcg gacaggggac caagctggaa ataaaacgga cggtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ttcgcccgtc acaaagagct tcaacagggg agagtgttaa    720
```

<210> SEQ ID NO 47
<211> LENGTH: 239
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 47

```
Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
            20                  25                  30

Val Thr Leu Gly Gln Pro Ala Ser Ile Ser Cys Lys Ser Ser Gln Ser
        35                  40                  45

Leu Ile Asp Ser Asp Gly Lys Thr Phe Leu Asn Trp Phe Gln Gln Arg
    50                  55                  60

Pro Gly Gln Ser Pro Arg Arg Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Gly Thr His Phe Pro Tyr Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 48
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Asn Tyr Pro Arg Asp Gly Ser Thr Lys Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Phe Cys
                85                  90                  95

Ala Lys Gly Phe Ile Thr Thr Val Pro Ser Ala Tyr Trp Gly Gln
            100                 105                 110

Gly Thr Leu Val Thr Val Ser Ala
        115                 120

```
<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49
```

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asn Tyr Gly Tyr Asp Tyr Ala Met Asp Tyr Trp Gly Gln Gly Thr
            100                 105                 110

Ser Val Thr Val Ser Ser
        115

```
<210> SEQ ID NO 50
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
            35                  40                  45

Gly Ala Ile Tyr Pro Gly Asp Ser Asp Thr Ser Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Tyr Tyr Gly Tyr Asp Trp Gly Gln Gly Thr Thr Val Thr
            100                 105                 110

Val Ser Ser
        115

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Lys Met Thr Gln Ser Pro Ser Ser Arg Tyr Ala Ser Leu Gly
1               5                   10                  15

Glu Arg Val Thr Ile Thr Cys Lys Ala Ser Gln Asp Ile Asn Arg Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105
```